United States Patent
Nishiuchi et al.

(10) Patent No.: US 12,318,253 B2
(45) Date of Patent: Jun. 3, 2025

(54) IMAGE DISPLAY DEVICE AND IMAGE DISPLAY METHOD

(71) Applicant: Asahi Intecc Co., Ltd., Seto (JP)

(72) Inventors: Makoto Nishiuchi, Seto (JP); Fumiyoshi Oshima, Seto (JP); Yuta Kubo, Seto (JP)

(73) Assignee: ASAHI INTECC CO., LTD., Seto (JP)

( * ) Notice: Subject to any disclaimer, the term of this patent is extended or adjusted under 35 U.S.C. 154(b) by 71 days.

(21) Appl. No.: 18/136,346

(22) Filed: Apr. 19, 2023

(65) Prior Publication Data

US 2023/0255595 A1 Aug. 17, 2023

Related U.S. Application Data

(63) Continuation of application No. PCT/JP2020/040072, filed on Oct. 26, 2020.

(51) Int. Cl.
*A61B 8/00* (2006.01)
*A61B 8/08* (2006.01)

(52) U.S. Cl.
CPC ............ *A61B 8/466* (2013.01); *A61B 8/0841* (2013.01); *A61B 8/4227* (2013.01); *A61B 8/4477* (2013.01); *A61B 8/483* (2013.01); *A61B 8/5207* (2013.01)

(58) Field of Classification Search
CPC ..... A61B 8/466; A61B 8/0841; A61B 8/4227; A61B 8/4477; A61B 8/483; A61B 8/5207; A61B 8/0875; A61B 8/0833; A61B 8/0891; A61B 8/4236; A61B 8/4494; A61B 8/462
See application file for complete search history.

(56) References Cited

U.S. PATENT DOCUMENTS

| | | |
|---|---|---|
| 2010/0191119 A1 | 7/2010 | Muthya et al. |
| 2010/0312120 A1 | 12/2010 | Meier |
| 2014/0081142 A1 | 3/2014 | Toma et al. |
| 2014/0303499 A1 | 10/2014 | Toma et al. |
| 2015/0230776 A1 | 8/2015 | Meier |
| 2020/0029931 A1 | 1/2020 | Kruse et al. |

FOREIGN PATENT DOCUMENTS

| | | |
|---|---|---|
| JP | S58-22046 A | 2/1983 |
| JP | 2002-541899 A | 12/2002 |
| JP | 2003-305039 A | 10/2003 |
| JP | 2006-051105 A | 2/2006 |
| JP | 2006-247214 A | 9/2006 |
| JP | 2010-269060 A | 12/2010 |
| WO | 00/62677 A1 | 10/2000 |

OTHER PUBLICATIONS

International Search Report and Written Opinion mailed on Nov. 24, 2020, received for PCT Application PCT/JP2020/040072, filed on Oct. 26, 2020, 10 pages including English Translation.

*Primary Examiner* — Christopher Koharski
*Assistant Examiner* — Zainab Mohammed Aldarraji
(74) *Attorney, Agent, or Firm* — XSENSUS LLP

(57) ABSTRACT

An image display device includes circuitry configured to acquire, from a human body, three-dimensional image information on an inside of the human body including a biological tube using a plurality of ultrasonic sensors, specify a position, in the biological tube, where a width of a longitudinal cross-section of the biological tube is maximum using transverse cross-section information on the biological tube included in the three-dimensional image information, generate an image representing the longitudinal cross-section of the biological tube at the position specified, and output the image generated to a display.

15 Claims, 21 Drawing Sheets

IMAGE DISPLAY DEVICE AND IMAGE DISPLAY METHOD

CROSS-REFERENCE TO RELATED APPLICATION

This application is a continuation application of International Application No. PCT/JP2020/040072 filed Oct. 26, 2020, the entire contents of which is incorporated herein by reference.

TECHNICAL FIELD

The present disclosure relates to an image display device and an image display method.

BACKGROUND ART

A technique is known that uses an ultrasonic wave to acquire, from a human body, information on the inside of the human body. For example, Patent literature 1 to 4 each discloses a diagnostic device in which an ultrasonic sensor (also referred to as "ultrasonic vibrator", "piezoelectric body", "ultrasonic transmitting/receiving element", or "ultrasonic element") is disposed in a sheet-shaped fixed member. Such a diagnostic device acquires, from the surface of the human body, information on the inside of the human body using an ultrasonic wave.

CITATION LIST

Patent Literature

Patent Literature 1: JP 2006-247214 A
Patent Literature 2: JP S58-22046 A
Patent Literature 3: JP 2006-51105 A
Patent Literature 4: JP 2010-269060 A

SUMMARY

Technical Problems

Further, it is known that a medical device such as a catheter is inserted into a biological lumen for a minimally invasive treatment or examination. In a procedure using such a medical device, the medical device should be prevented from contacting an inner wall of the biological tube as much as possible in order to prevent a damage to a biological tissue (e.g., a blood vessel wall, etc.). However, the techniques described in Patent literatures 1 to 4 can merely specify the position of the biological tube (e.g., a blood vessel) inside the human body without presenting the state of the biological tube or the positional relationship between the biological tube and the medical device to an operator. Thus, the techniques described in Patent literatures 1 to 4 still have the problem in that it is necessary to rely on the operator's sense for pushing forward the medical device inside the biological lumen.

Note that such a problem is generally common across medical devices such as a catheter, a guide wire, and an endoscope which are inserted into an organ (biological tube) in the human body such as a vascular system, a lymphatic system, a biliary system, a urinary system, a respiratory system, a digestive system, a secretory gland, or a reproductive organ.

Embodiments are directed to solving at least a part of the above and other problems, by providing an image display presenting a state of a biological tube to an operator.

Solutions to Problems

Embodiments are directed to solving at least a part of the above and other problems and can be implemented as the following aspects.

(1) According to one aspect, an image display device is provided. This image display device includes an acquisition portion that acquires, from a human body, three-dimensional image information on the inside of the human body including a biological tube using a plurality of ultrasonic sensors, a position specification portion that specifies a position, in the biological tube, where a width of a longitudinal cross-section of the biological tube is maximum using transverse cross-section information on the biological tube included in the three-dimensional image information, an image generation portion that generates an image representing the longitudinal cross-section of the biological tube at the position specified by the position specification portion, and a display portion that displays the image generated by the image generation portion.

According to this configuration, the position specification portion specifies the position, in the biological tube, where the width of the longitudinal cross-section of the biological tube is maximum using the transverse cross-section information on the biological tube included in the three-dimensional image information. The image generation portion generates the image representing the longitudinal cross-section of the biological tube at the position specified by the position specification portion. The display portion displays the image generated by the image generation portion. In this manner, the operator can recognize the state of the biological tube by referring to the image representing the longitudinal cross-section of the biological tube displayed in the display portion. As a result, it is possible to provide the image display device capable of presenting the state of the biological tube to the operator. Further, in order to prevent the medical devices such as a catheter from contacting the inner wall of the biological tube and damaging the biological tissue (e.g., a blood vessel wall, etc.), the medical device may be delivered while being positioned near the center of the biological lumen. In this regard, according to the present configuration, the image displayed in the display portion represents the longitudinal cross-section of the biological tube at the position where the width of the longitudinal section of the biological tube is maximum, in other words, the longitudinal cross-section of the biological tube including the center of the biological lumen. Thus, the operator can recognize the state of the biological tube corresponding to the position through which the medical device is to be passed.

(2) In the image display device of the above aspect, the three-dimensional image information may include three-dimensional image information on the medical device inserted into a biological lumen. In a case where the medical device is present at the position specified by the position specification portion, the image generation portion may generate an image including the longitudinal cross-section of the biological tube and the medical device. In a case where the medical device is not present at the position specified by the position specification portion, the image generation portion may generate an image including the longitudinal cross-section of the biological tube but not including the medical device.

According to this configuration, the image generation portion generates the image including the longitudinal cross-section of the biological tube and the medical device in the case where the medical device is present at the position specified by the position specification portion, and the image generation portion generates the image including the longitudinal cross-section of the biological tube but not including the medical device in the case where the medical device is not present at the position specified by the position specification portion. Thus, the operator can recognize the positional relationship between the biological tube and the medical device by determining whether the medical device is included in the image displayed in the display portion. Specifically, if the medical device is included in the image, the operator can recognize that the medical device is present at the position where the longitudinal cross-section width of the biological tube is maximum (in other words, the medical device is present near the center of the biological lumen). Further, if the medical device is not included in the image, the operator can recognize that the medical device is not present at the position where the longitudinal cross-section width of the biological tube is maximum (in other words, the medical device is close to the inner wall of the biological tube). As a result, according to the present configuration, it is possible to provide the image display device capable of presenting to the operator not only the state of the biological tube but also the positional relationship between the biological tube and the medical device.

(3) In the image display device of the above aspect, the plurality of ultrasonic sensors may be disposed so as to surround the human body.

According to this configuration, the plurality of ultrasonic sensors are disposed as to surround the human body. Thus, the acquisition portion can acquire the three-dimensional image information in the entire range surrounded by the ultrasonic sensors. As a result, the image display device can determine any biological tube from the entire range and generate and display the image representing the longitudinal cross-section of the biological tube.

(4) In the image display device of the above aspect, the plurality of ultrasonic sensors may be ultrasonic elements disposed inside the entire circumference of a belt-shaped body that surrounds the human body.

According to this configuration, the plurality of ultrasonic sensors are disposed inside the entire circumference of the belt-shaped body that surrounds the human body. Thus, the ultrasonic sensors can be easily attached to and removed from a patient regardless of the patient's physique (body size).

(5) In the image display device of the above aspect, the position specification portion may specify, in each of a plurality of positions of the biological tube, a position where the longitudinal cross-section width of the biological tube is maximum. The image generation portion may generate the images representing the longitudinal cross-sections of the biological tube at the plurality of positions identified by the position specification portion.

According to this configuration, the position specification portion specifies, in each of the plurality of positions of the biological tube, the position where the longitudinal cross-section width of the biological tube is maximum. The image generation portion generates the images representing the longitudinal cross-sections of the biological tube at the plurality of positions. As a result, the image display device can generate and display the image representing the longitudinal cross-section of the biological tube regardless of the shape of the biological tube by appropriately setting the position according to the shape of the biological tube (e.g., curving, branching, etc.).

It should be noted that the present invention can be implemented in various aspects. For example, the present invention can be implemented in the form of an image generation device that generates an image for display, an image generation method, a medical system including an image display device, methods for producing these devices and systems, computer programs that achieve functions of these devices and systems, and the like.

DETAILED DESCRIPTION

First Embodiment

Figure 1:
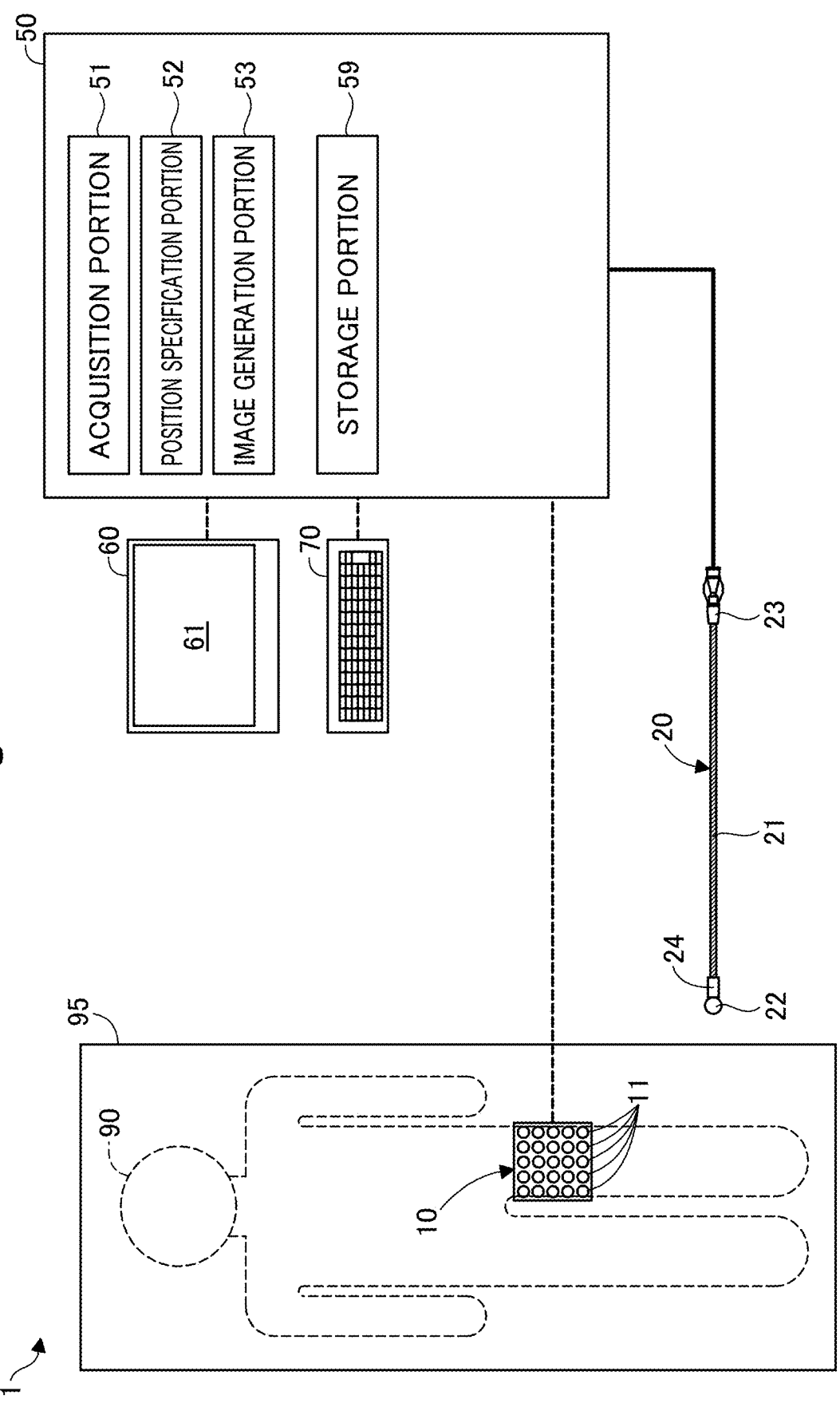
FIG. 1 is an explanatory diagram illustrating an example of a configuration of an image display device of a first embodiment.

FIG. 1 is an explanatory diagram illustrating an example of a configuration of an image display device 1 of a first embodiment. The image display device 1 is a device that uses an ultrasonic wave to generate and display an image representing a longitudinal cross-section of a biological tube of a human body 90. Hereinafter, a blood vessel of the human body 90 will be described as an example of the biological tube. However, the biological tube may include, in addition to a blood vessel system, a lymphatic system, a biliary system, a urinary system, a respiratory system, a digestive system, a secretory gland, a reproductive organ, and the like. Further, the image display device 1 can be used in combination with a medical device. Hereinafter, a catheter 20 will be described as an example of the medical device. However, in addition to the catheter 20, any device, e.g., a guide wire, can be adopted as the medical device. The image display device 1 includes an ultrasonic sensor array 10, a computer 50, a display 60, and an input device 70.

Figure 2:
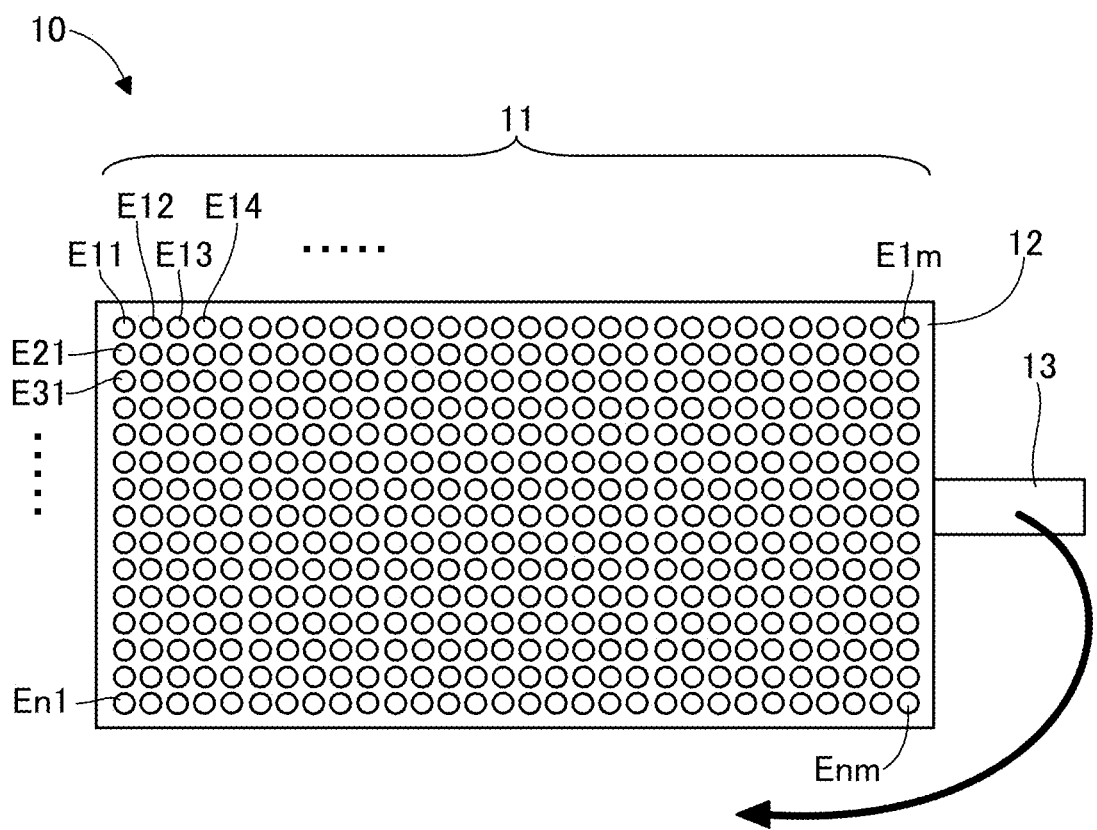
FIG. 2 is an explanatory diagram illustrating an example of a configuration of an ultrasonic sensor array.

FIG. 2 is an explanatory diagram illustrating an example of a configuration of the ultrasonic sensor array 10. The ultrasonic sensor array 10 includes a plurality of ultrasonic sensors 11 and is used to acquire three-dimensional image information on the inside of the human body 90 including the biological tube. The ultrasonic sensor array 10 includes the plurality of ultrasonic sensors 11, a belt-shaped body 12, and a band 13.

The ultrasonic sensor 11 is an ultrasonic probe (also referred to as "ultrasonic vibrator", "piezoelectric body", "ultrasonic transmitting/receiving element", or "ultrasonic element") that transmits an ultrasonic wave toward a biological tissue inside the human body 90 and receives the ultrasonic wave which has been propagated through and reflected by the biological tissue. In the example of FIG. 2, the plurality of ultrasonic sensors 11 are arranged in a grid pattern in row n and column m (where n and m are any natural number) on the entire surface on one side of the belt-shaped body 12. Hereinafter, the surface of the belt-shaped body 12 on which the ultrasonic sensors 11 are disposed is also referred to as "inner surface", while the surface opposite to the inner surface is also referred to as "outer surface". Note that, in FIG. 2, the ultrasonic sensor in row 1 and column 1 is represented by E11, the ultrasonic sensor in row 1 and column 2 is represented by E12, and the ultrasonic sensor in row 1 and column m is represented by E1$m$, and the ultrasonic sensor in row n and column m is represented by Enm. Note that, although the ultrasonic sensors 11 are arranged regularly in the grid pattern in row n and column m, the ultrasonic sensors 11 may be arranged irregularly.

The belt-shaped body 12 is a belt-shaped member having flexibility and stretchability. The belt-shaped body 12 is made of, for example, rubber, a synthetic resin, cloth, or the like. The operator wraps the belt-shaped body 12 around the human body 90 lying on a bed 95 with the inner surface (surface on which the ultrasonic sensors 11 are disposed) of the belt-shaped body 12 facing a body surface side of the human body 90. This allows the plurality of ultrasonic sensors 11 to be positioned so as to surround the human body 90. Note that, in the example of FIG. 1, the belt-shaped body 12 is wrapped around the thigh of a human body 90. However, the belt-shaped body 12 may be wrapped around the chest, abdomen, waist, leg, arm, neck, head, or anywhere else. Further, a lubricant maybe provided between the belt-shaped body 12 is and the body surface (skin) of the human body 90.

The band 13 is a small strip attached to one short edge of the belt-shaped body 12. For example, the band 13 is made of rubber, a synthetic resin, cloth, or the like. The band 13, which is provided with a metal fitting for fixing, a magic tape, or the like, allows the belt-shaped body 12 to be fixed in a state in which the belt-shaped body 12 is wrapped around the human body 90.

Returning to FIG. 1, the explanation will be continued. The catheter 20 is a medical device that is inserted into a biological lumen (into a blood vessel) of the human body 90 and used for treatment or examination. The catheter 20 includes a shaft 21, a distal tip 22, a connector 23, and a marker 24. The shaft 21 is a hollow member having an elongated outer shape. The distal tip 22 is a flexible member attached to a distal end of the shaft 21. The connector 23 is a member provided at a proximal end of the shaft 21 and used by the operator to hold the catheter 20. The marker 24 is a member having radiopacity provided between the shaft 21 and the distal tip 22. Note that the configuration of the catheter 20 shown in FIG. 1 is merely an example, and any configuration can be adopted. For example, the distal tip 22 or the marker 24 may be omitted. For example, instead of the catheter 20, a guide wire or the like may be used.

The display 60 may be a liquid crystal display including a display screen 61. The display 60 functions as a "display" that displays an image generated by an image generation portion 53 described below. Note that the display 60 may be configured by a display device other than the liquid crystal display (e.g., smart glasses, a projector, an OLED display, etc.). The input device 70 is a keyboard and a mouse for inputting information to the computer 50. Note that the input device 70 may be configured by an input device other than the keyboard and the mouse (e.g., a microphone for acquiring voice input, a touch panel, a foot switch, a camera for detecting gestures, a joystick, etc.).

The computer 50 is a device that controls the image display device 1 as a whole. The computer 50 is configured by including a CPU (Central Processing Unit), a ROM (Read Only Memory), and a RAM (Random access memory) and functions as an acquisition portion 51, a position specification portion 52, and an image generation portion 53 by the CPU executing a computer program stored in the ROM. Further, the computer 50 includes a hard disk, a flash memory, a memory card, or the like, which functions as a storage portion 59, i.e., a non-transitory computer readable storage device. The computer 50 is electrically connected to each of the ultrasonic sensor array 10, the display 60, and the operation portion 70.

As used herein 'computer' refers to circuitry that may be configured via the execution of computer readable instructions, and the circuitry may include one or more local processors and/or one or more remote processors, such as a cloud computing resource, or any combination thereof.

Figure 3:
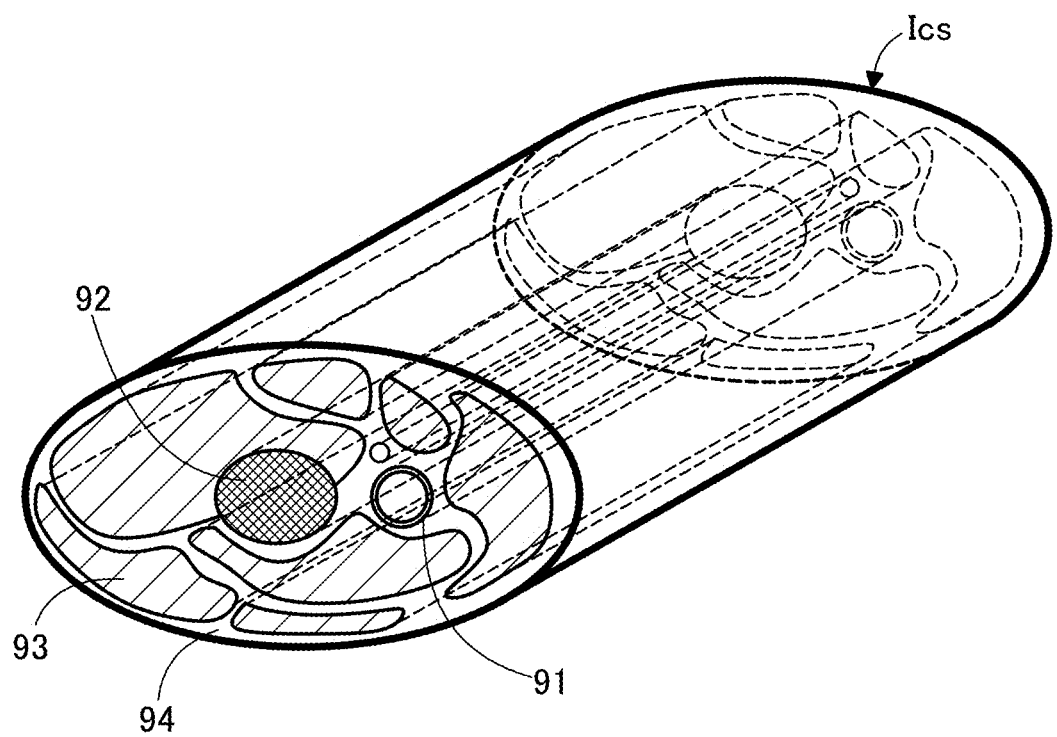
FIG. 3 is an explanatory diagram illustrating three-dimensional image information on a human body.

FIG. 3 is an explanatory diagram of three-dimensional image information Ics on the human body 90. The acquisition portion 51 acquires, from the human body 90, the three-dimensional image information Ics on the inside of the human body including a blood vessel 91 using the ultrasonic sensors 11 (E11 to Enm) of the ultrasonic sensor array 10 wrapped around the human body 90. The three-dimensional image information Ics is information representing a stereoscopic internal structure of the human body 90. The three-dimensional image information Ics includes a relative three-dimensional position of biological tissues inside the human body 90, such as the blood vessel 91, a bone 92, a muscle 93, and a fat 94, and a three-dimensional shape of each of the biological tissues. The blood vessel 91 corresponds to the "biological tube". Further, when the three-dimensional image information Ics is acquired with the catheter 20 inserted into the human body 90, the three-dimensional image information Ics includes the three-dimensional position of the catheter 20 inside the human body 90 and the three-dimensional shape of the catheter 20. Note that the three-dimensional image information Ics may include the biological tube different from the blood vessel 91, such as, for example, a lymphatic vessel.

The acquisition portion 51 controls the transmission timing of ultrasonic waves in the plurality of ultrasonic sensors 11 (E11 to Enm) and thereby shift the transmission timing of ultrasonic waves for each of the ultrasonic sensors E11, E12, E13, . . . , Enm. As a result, the timing of ultrasonic waves (reflected waves) received by each sensor is also shifted, allowing the acquisition portion 51 to acquire the reflected waves with intensities corresponding to the positions of the ultrasonic sensors E11 to Enm. Each biological tissue inside the human body 90, such as the blood vessel 91, the bone 92, the muscle 93, or the fat 94, has a different acoustic impedance value. The acquisition portion 51 can acquire distribution of the biological tissues inside the human body 90 (distribution of tissues such as the blood vessel 91, the bone 92, the muscle 93, the fat 94, etc.) from the intensities of the reflected waves received by the plurality of ultrasonic sensors 11 (E11 to Enm) and generate the three-dimensional image information Ics shown in FIG. 3.

Figure 4:
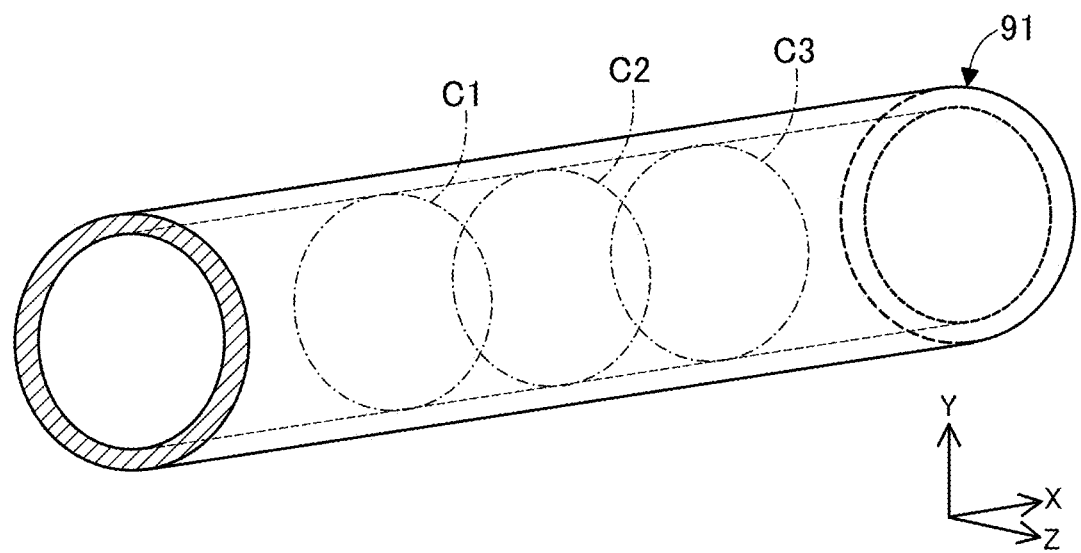
FIG. 4 is an explanatory diagram illustrating a blood vessel included in the three-dimensional image information.

FIG. 4 is an explanatory diagram of the blood vessel 91 included in the three-dimensional image information Ics. Mutually perpendicular XYZ axes are shown in FIG. 4. The X-axis corresponds to a length direction of the blood vessel 91, and the Y-axis and Z-axis each corresponds to a width direction of the blood vessel 91. The position specification portion 52 specifies a position where the longitudinal cross-section width of the blood vessel 91 is maximum from the three-dimensional image information Ics.

Specifically, first, the position specification portion 52 specifies the blood vessel 91 to be displayed as an image from the three-dimensional image information Ics. FIG. 4 shows an example of the blood vessel 91 specified by the position specification portion 52. The specification of the blood vessel 91 can be achieved by instruction of the operator via the operation portion 70. Further, the blood vessel 91 may be specified automatically by pattern matching between the shape of each biological tissue included in the three-dimensional image information Ics and the shape stored in the storage portion 59 in advance. Next, the position specification portion 52 acquires a transverse cross-section of the blood vessel 91 at a freely determined position of the specified blood vessel 91. In the example of FIG. 4, the position specification portion 52 acquires three transverse cross-sections, a transverse cross-section C2 at the approximate center of the blood vessel 91 and transverse cross-sections C1 and C3 shifted from the transverse cross-section C2 in the ±X-axis directions. Note that the position and the number of the transverse cross-sections acquired by the position specification portion 52 can be freely changed. For example, the position specification portion 52 may acquire only one transverse cross-section of the blood vessel 91.

Figure 5:
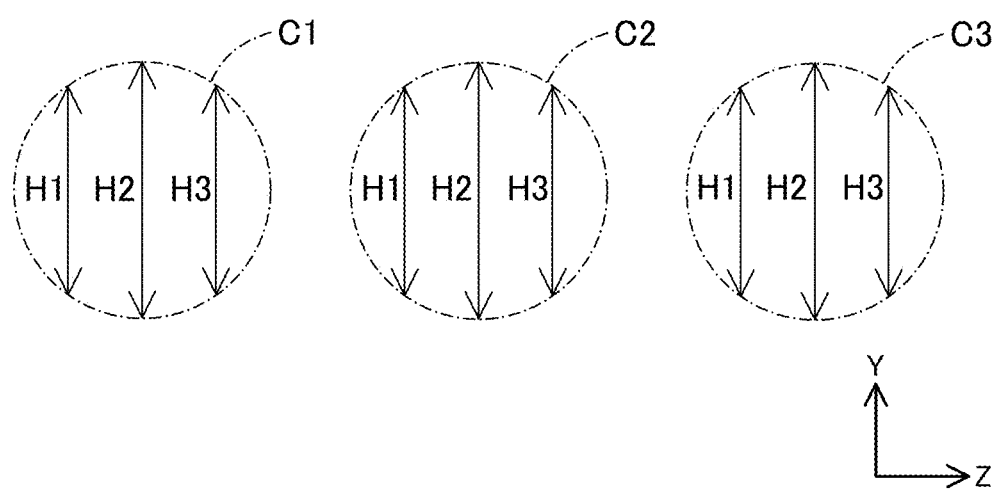
FIG. 5 is a diagram describing a process in a position specification portion.

FIG. 5 is a diagram describing a process in the position specification portion 52. The YZ axes in FIG. 5 correspond to the YZ axes in FIG. 4. The position specification portion 52 specifies the position where the longitudinal cross-section width of the blood vessel 91 is maximum in the blood vessel 91 using the acquired transverse cross-sections C1 to C3. Specifically, the position specification portion 52 specifies, for each of the acquired transverse cross-sections C1 to C3, a maximum width (a width H2 in the example of FIG. 5) among widths H1 to Hx (where x is any natural number) in the Y-axis direction. The position of the width H2 specified in this process corresponds to the position where the longitudinal cross-section width of the blood vessel 91 is maximum. Note that, in FIG. 5, only the widths H1, H2, and H3 of the widths H1 to Hx in the Y-axis direction are shown for the transverse cross-sections C1 to C3.

Figure 6:
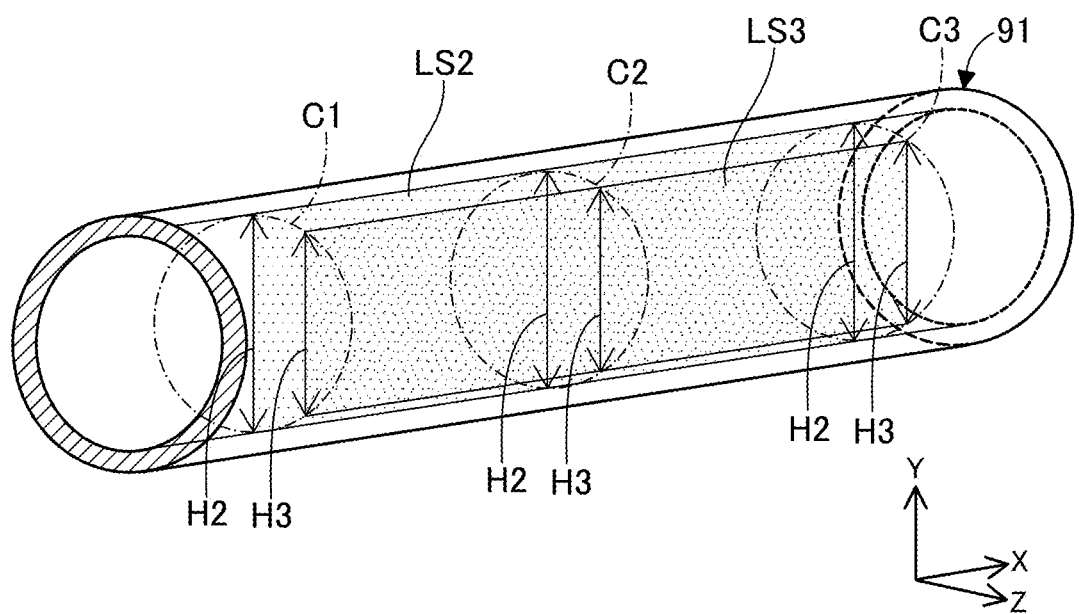
FIG. 6 is a diagram describing a process in an image generation portion.
Figure 7:
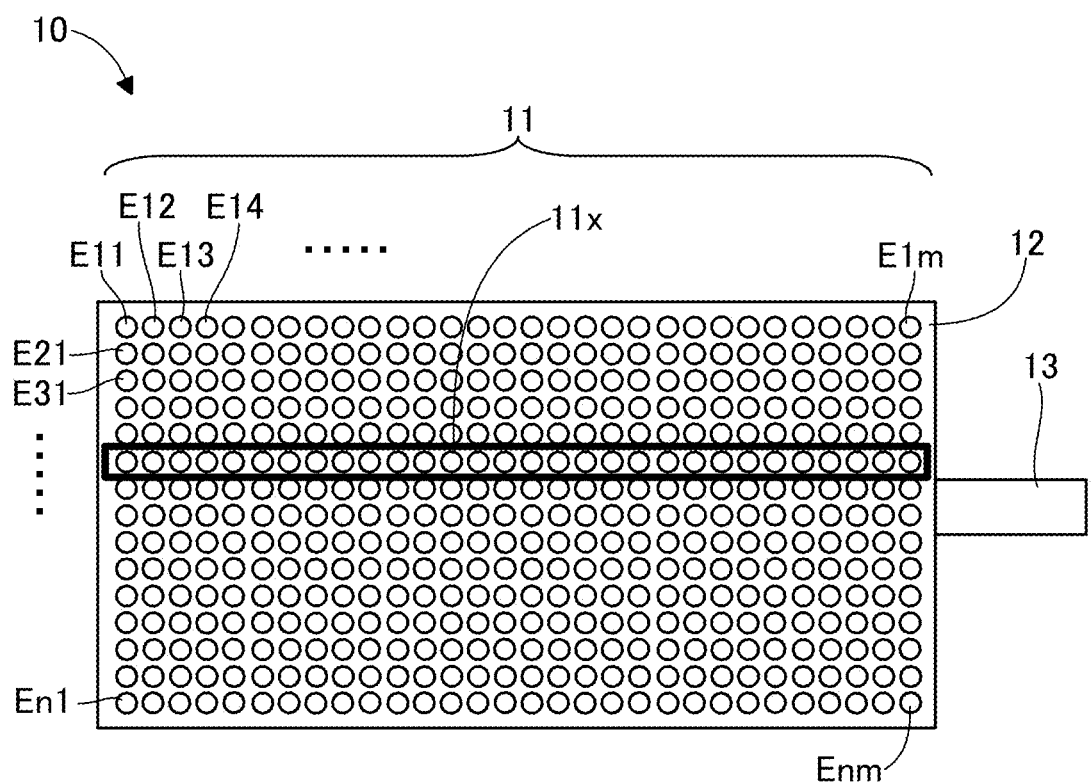
FIG. 7 is a diagram describing the process in the image generation portion.

FIG. 6 and FIG. 7 are diagrams describing a process in the image generation portion 53. The XYZ axes in FIG. 6 correspond to the XYZ axes in FIG. 4. The image generation portion 53 generates an image representing the longitudinal cross-section LS2 of the blood vessel 91 at the position specified by position specification portion 52 (i.e., the position of the width H2 where the width in the Y-axis direction is maximum for each of the transverse cross-sections C1 to C3). Specifically, the image generation portion 53 uses the reflected waves received by the ultrasonic sensors $11x$ (FIG. 7: rectangular frame), of the plurality of ultrasonic sensors 11 (E11 to Enm) of the ultrasonic sensor array 10 shown in FIG. 7, at the positions corresponding to the longitudinal cross-section LS2 to generate a two-dimensional image with gradation scales according to the intensity of the reflected wave at each of the ultrasonic sensors $11x$. Then, the image generation portion 53 causes the display 60 to display the generated image.

Figure 8A:
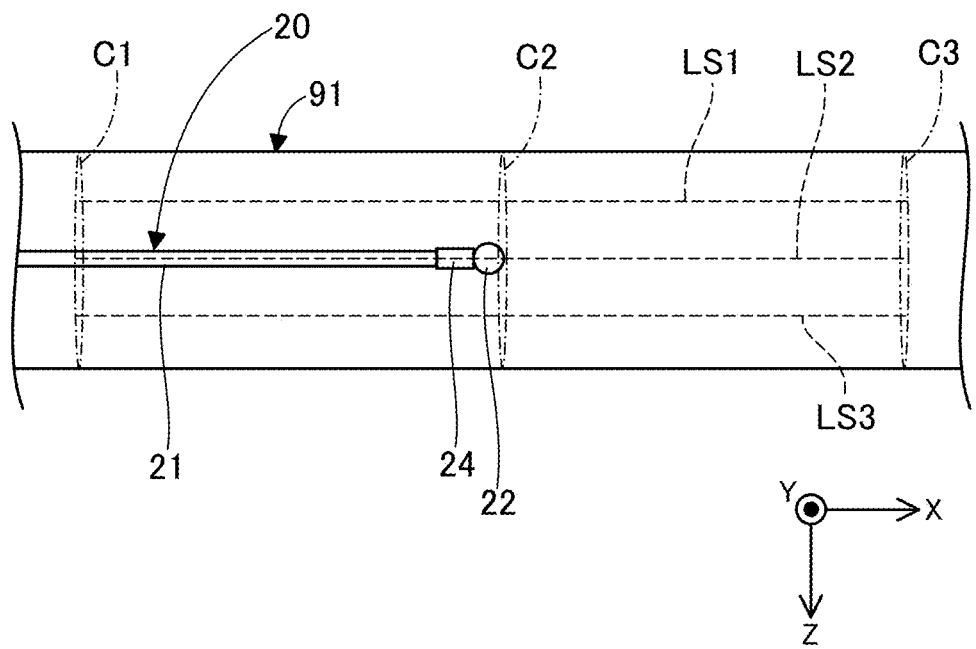
FIGS. 8A and 8B are diagrams illustrating an example of an image displayed in a display portion.
Figure 8B:
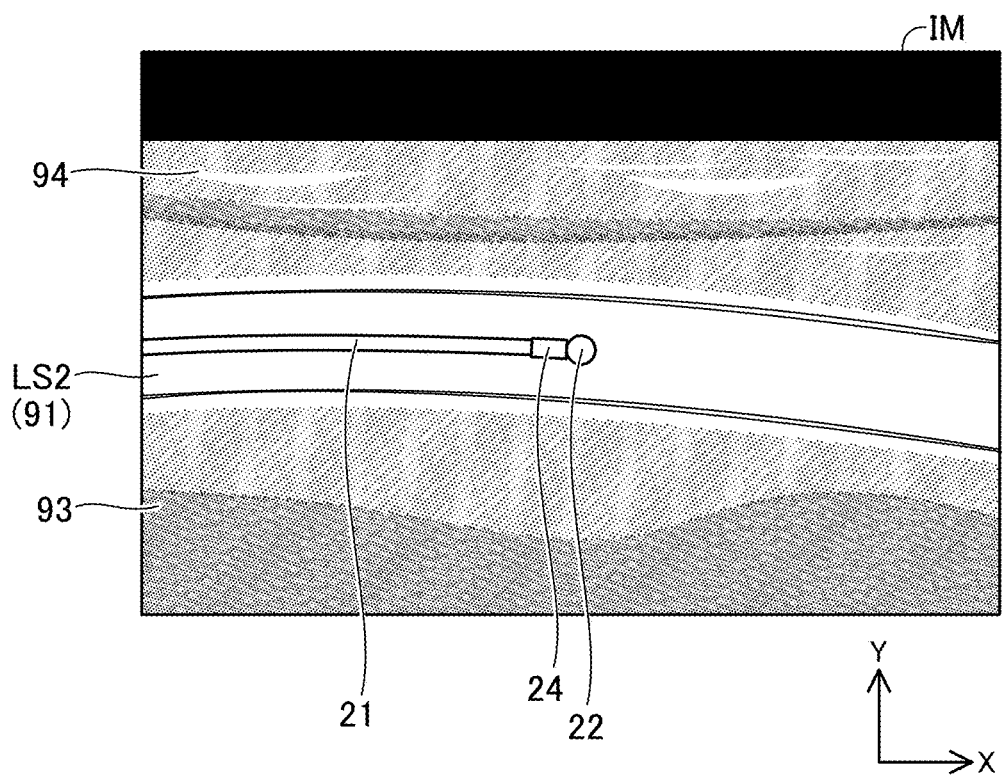

FIGS. 8A and 8B are diagrams illustrating an example of the image displayed in the display 60. FIG. 8A shows the positional relationship between the blood vessel 91 and the catheter 20 viewed from the Y-axis direction, and FIG. 8B shows an example of an image IM displayed in the display 60 in this situation. The image IM is a two-dimensional image representing an XY plane including the longitudinal cross-section LS2. As shown in FIG. 8A, when the catheter 20 is advancing near the longitudinal cross-section LS2 of the blood vessel 91, the image IM representing the longitudinal cross-section LS2 of the blood vessel 91 includes the catheter 20 (the shaft 21, the marker 24, and the distal tip 22). Further, the image IM also includes other biological tissues such as the muscle 93 and the fat 94.

Figure 9A:
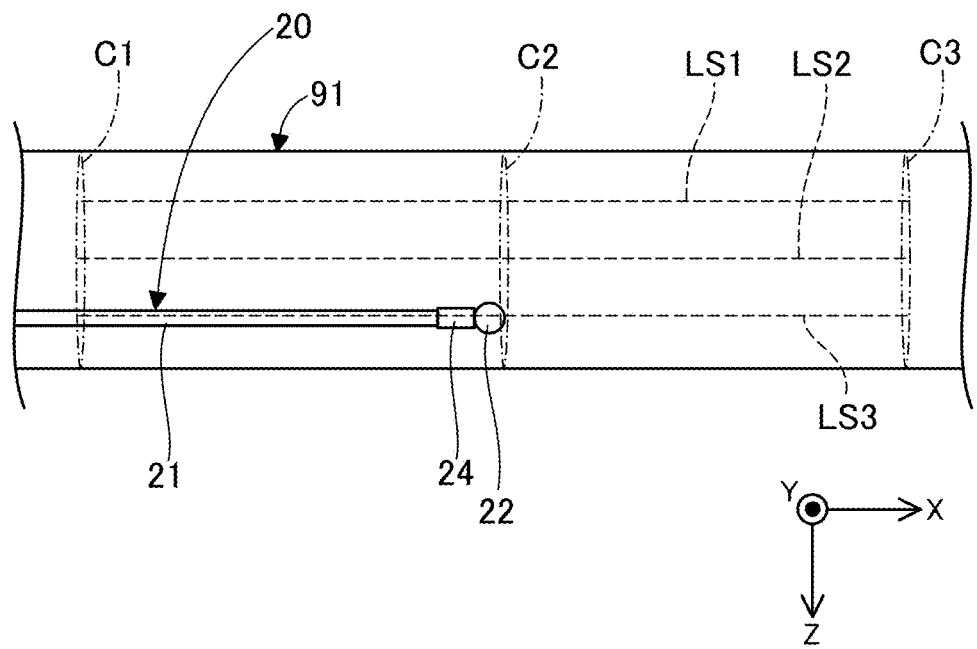
FIGS. 9A and 9B are diagrams illustrating another example of the image displayed in the display portion.
Figure 9B:
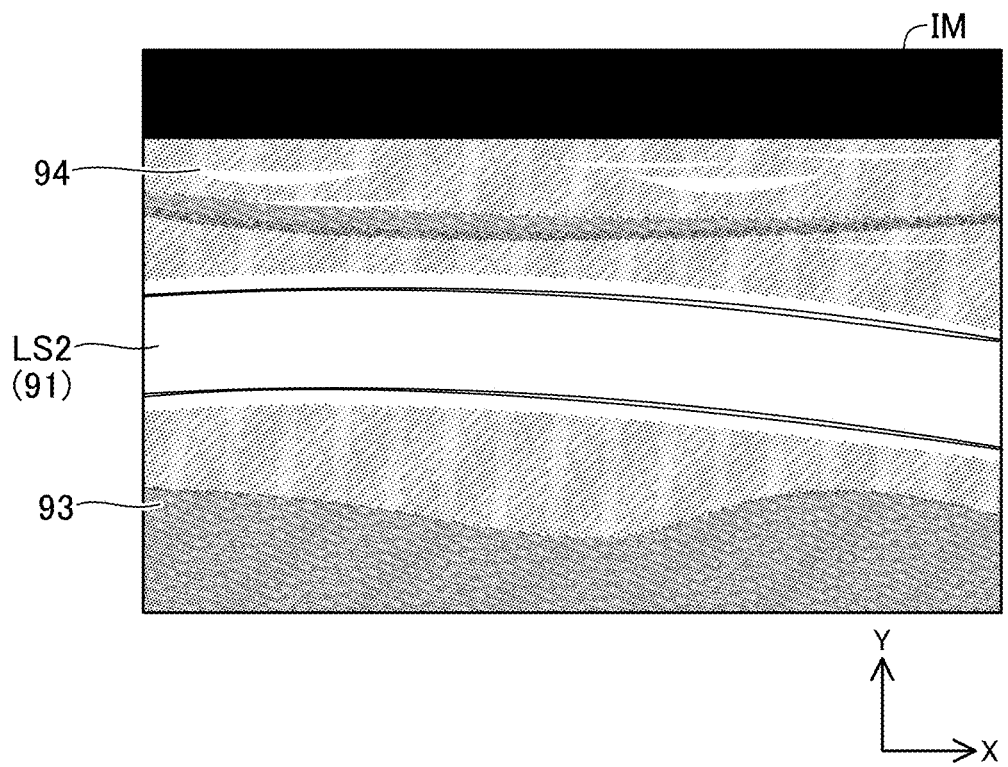

FIGS. 9A and 9B are diagrams illustrating another example of the image displayed in the display 60. The configurations in FIGS. 9A and 9B are the same as those in FIGS. 8A and 8B. As shown in FIG. 9A, when the catheter 20 is advancing at a position away from the longitudinal cross-section LS2 of the blood vessel 91 (in the shown example, a position near a longitudinal cross-section LS3), the image IM representing the longitudinal cross-section LS2 of the blood vessel 91 does not include the catheter 20.

Figure 10A:
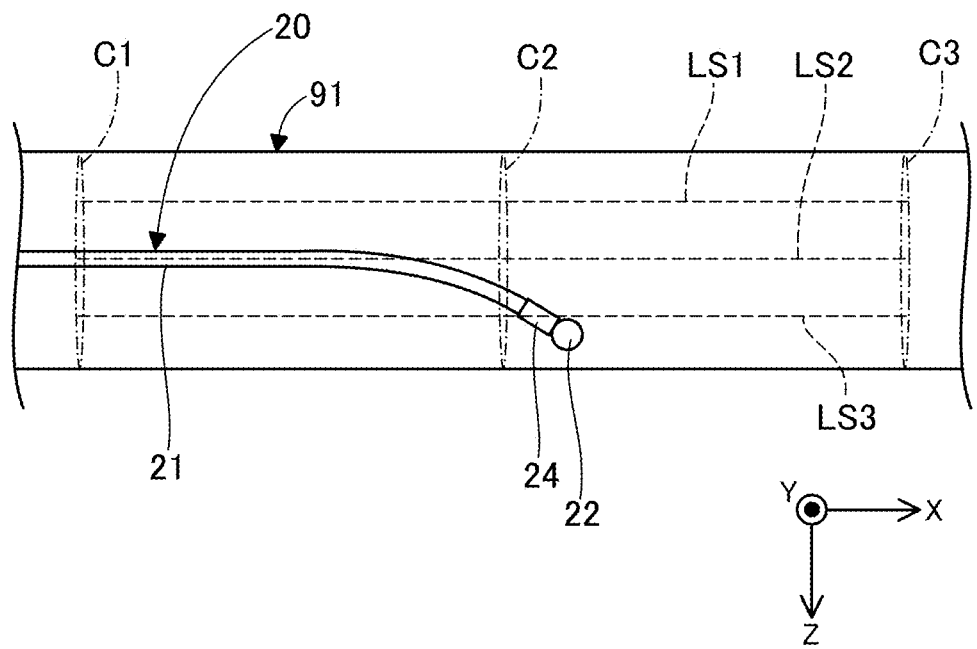
FIGS. 10A and 10B are diagrams illustrating yet another example of the image displayed in the display portion.
Figure 10B:
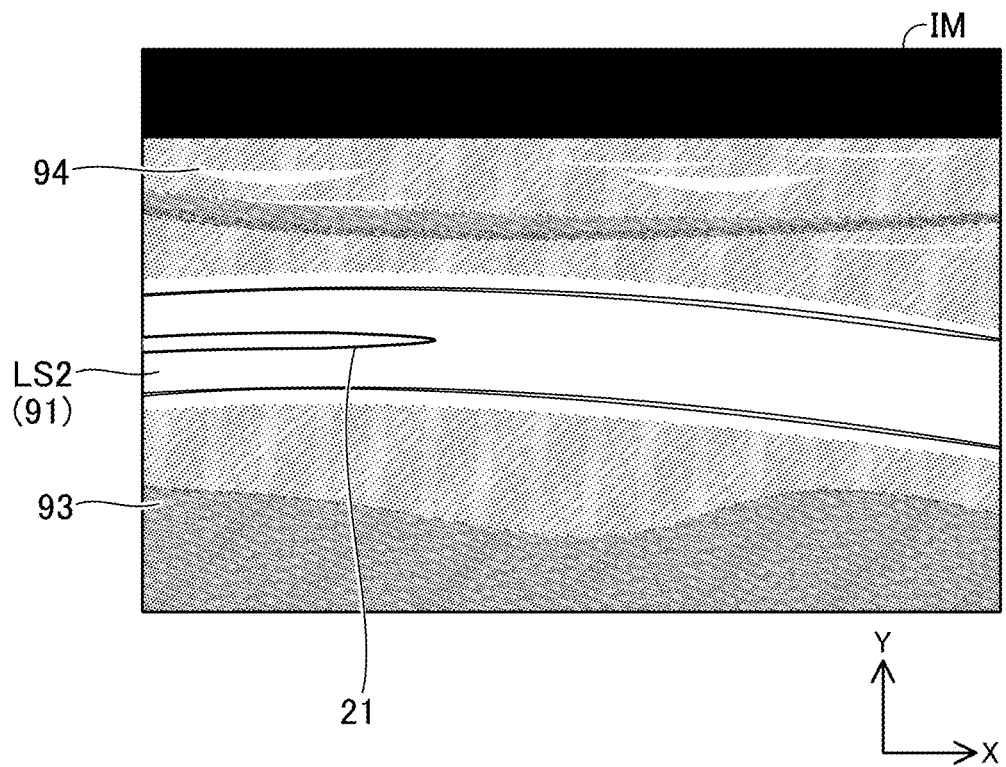

FIGS. 10A and 10B are diagrams illustrating yet another example of the image displayed in the display 60. The configurations in FIGS. 10A and 10B are the same as those in FIGS. 8A and 8B. As shown in FIG. 10A, a part of the catheter 20 on the distal side is curved and present at a position away from the longitudinal cross-section LS2 of the blood vessel 91, and a part on the proximal side is present at a position near the longitudinal cross-section LS2 of the blood vessel 91. In such a case, the image IM representing the longitudinal cross-section LS2 of the blood vessel 91 does not include the part of the catheter 20 on the distal side but includes the part on the proximal side.

As described above, the longitudinal cross-section LS2 of the blood vessel 91 corresponds to the position H2 where the longitudinal cross-section width of the blood vessel 91 is maximum (in a case of the blood vessel 91 having a substantially circular transverse cross-sectional shape shown in FIG. 5, the center in the Z-axis direction). As shown in FIG. 8B, the operator pushes forward the catheter 20 such that the catheter 20 passes through the center of the blood vessel 91 in the Y-axis direction in the image IM including the catheter 20. In this manner, the operator can push forward the catheter 20 at the center of the blood vessel 91 (in other words, at the farthest position from the inner wall of the blood vessel 91). Further, with the image display device 1, the image IM of the blood vessel 91 and the catheter 20 can be confirmed in real time using the ultrasonic waves. Thus, compared with imaging by X-ray photography, there is no need to inject a contrast medium into the body, making it possible to reduce the burden on the human body 90 and improve the safety of the procedure. Further, compared with imaging by CT scan, the image IM of the blood vessel 91 and the catheter 20 can be obtained in real time, making it possible to reduce the time required for the procedure.

As described above, according to the image display device 1 of the first embodiment, the position specification portion 52 uses the transverse cross-section information C1 to C3 of the biological tube (blood vessel 91) included in the three-dimensional image information Ics to specify the position H2 where the longitudinal cross-section width of the biological tube is maximum in the biological tube, the image generation portion 53 generates the image IM representing the longitudinal cross-section LS2 of the biological tube at the position H2 specified by the position specification portion 52, and the display 60 displays the image IM generated by the image generation portion 53 (FIGS. 8A and 8B to FIGS. 10A and 10B). In this manner, the operator can recognize the state of the biological tube by referring to the image IM representing the longitudinal cross-section LS2 of the biological tube displayed in the display 60. As a result, it is possible to provide the image display device 1 capable of presenting the state of the biological tube to the operator. Further, in order to prevent the medical device such as the catheter 20 from contacting the inner wall of the biological tube and damaging the biological tissue (e.g., a blood vessel wall, etc.), the medical device may delivered while being positioned near the center of the biological lumen. In this regard, according to the image display device 1 of the first embodiment, the image IM displayed in the display 60 represents the longitudinal cross-section LS2 of the biological tube at the position H2 where the longitudinal cross-section width of the biological tube is maximum, in other words, the longitudinal cross-section LS2 of the biological tube including the center of the biological lumen. Thus, the operator can recognize the state of the biological tube corresponding to the position through which the medical device is to be passed.

Further, when the medical device (catheter 20) is present at the position H2 specified by the position specification portion 52, the image display device 1 of the first embodiment generates the image IM including the longitudinal cross-section LS2 of the biological tube (blood vessel 91) and the medical device (FIGS. 8A and 8B and FIGS. 10A and 10B). Further, when the medical device is not present at the position H2 specified by the position specification portion 52, the image display device 1 generates the image IM including the longitudinal cross-section LS2 of the biological tube but not including the medical device (FIGS. 9A and 9B and FIGS. 10A and 10B). In this manner, the operator can recognize the positional relationship between the biological tube and the medical device by determining whether the image IM displayed in the display 60 includes the medical device. Specifically, if the medical device is included in the image IM, the operator can recognize that the medical device is present at the position H2 where the longitudinal cross-section width of the biological tube is maximum (in other words, the medical device is positioned near the center of the biological lumen). Further, if the medical device is not included in the image IM, the operator can recognize that the medical device is not present at the position H2 where the longitudinal cross-section width of the biological tube is maximum (in other words, the medical device is near the inner wall of the biological tube). As a result, according to the image display device 1 of the first embodiment, it is possible to provide the image display device 1 capable of presenting, in addition to the state of the biological tube, the positional relationship between the biological tube and the medical device to the operator.

Further, according to the image display device 1 of the first embodiment, the position specification portion 52 specifies the position H2 where the longitudinal cross-section width of the biological tube is maximum at each of a plurality of positions C1 to C3 of the biological tube (blood vessel 91), and the image generation portion 53 generates the image IM representing the longitudinal cross-section LS2 of the biological tube at the plurality of positions C1 to C3 (passing across the plurality of positions C1 to C3). As a result, the image display device 1 can generate and display the image IM representing the longitudinal cross-section LS2 of the biological tube by appropriately setting the positions C1 to C3 according to the shape of the biological tube (e.g., curving, branching, etc.) regardless of the shape of the biological tube.

Further, in the image display device 1 of the first embodiment, the plurality of ultrasonic sensors 11 (E11 to Enm) are disposed so as to surround the human body 90 (FIG. 1). Thus, the acquisition portion 51 can acquire the three-dimensional image information Ics in the entire range surrounded by the ultrasonic sensors 11. As a result, the image display device 1 can determine any biological tube (blood vessel 91) from the entire range and generate and display the image IM representing the longitudinal cross-section LS2 of the biological tube. Further, the plurality of ultrasonic sensors 11 are disposed inside the entire circumference of the belt-shaped body 12 that surrounds the human body 90 (FIG. 2). Thus, the ultrasonic sensor array 10 can be easily attached to and removed from the patient, and the common ultrasonic sensor array 10 can be used regardless of the patient's physique (body size).

Second Embodiment

Figure 11:
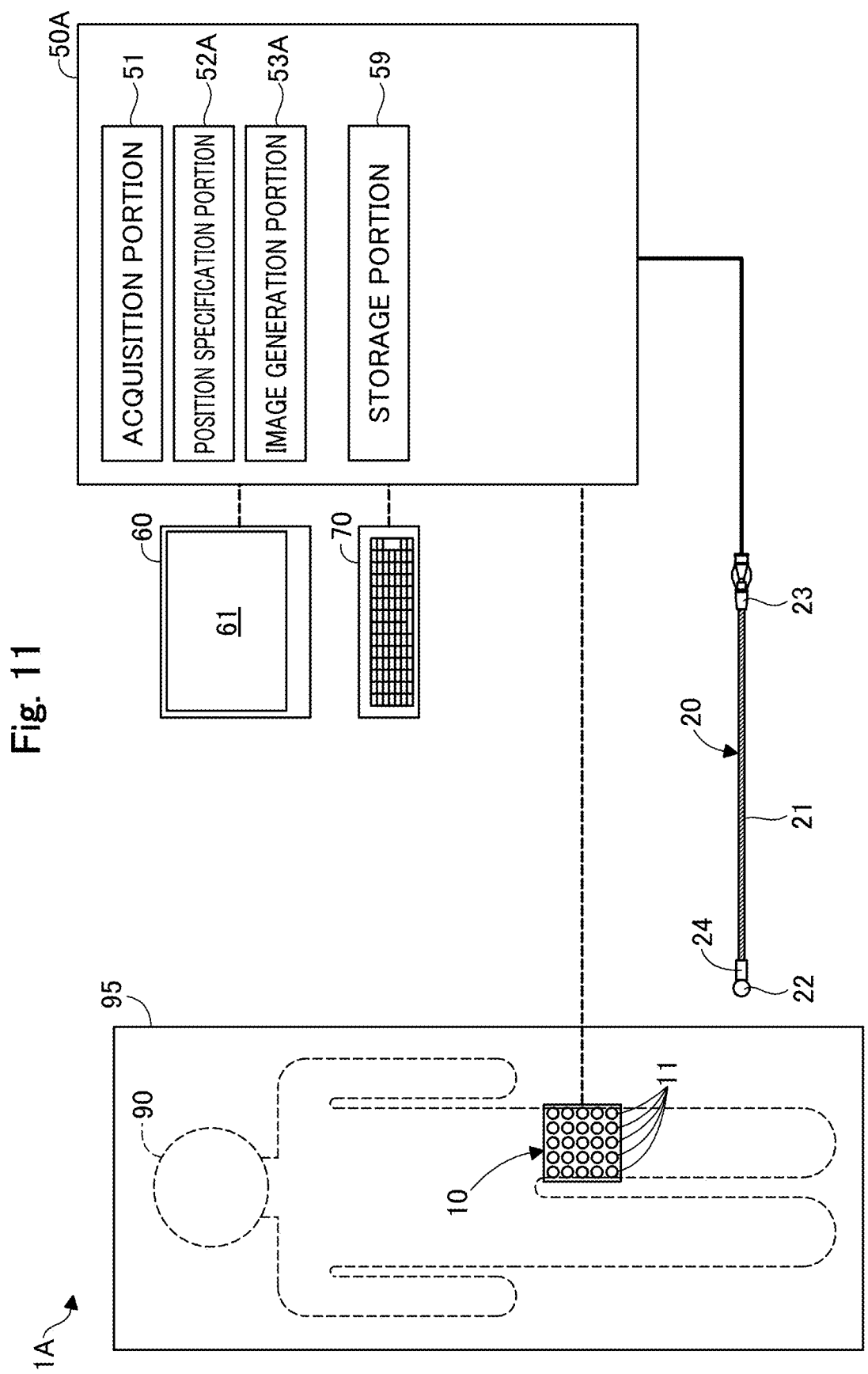
FIG. 11 is an explanatory diagram illustrating an example of a configuration of the image display device of a second embodiment.

FIG. 11 is an explanatory diagram illustrating an example of a configuration of an image display device 1A of a second embodiment. The image display device 1A of the second embodiment can generate and display an image corresponding to a shape change such as curving or branching of the biological tube. The image display device 1A includes a computer 50A instead of the computer 50 in the configuration of the first embodiment. The computer 50A includes a position specification portion 52A instead of the position specification portion 52 and an image generation portion 53A instead of the image generation portion 53.

Figure 12:
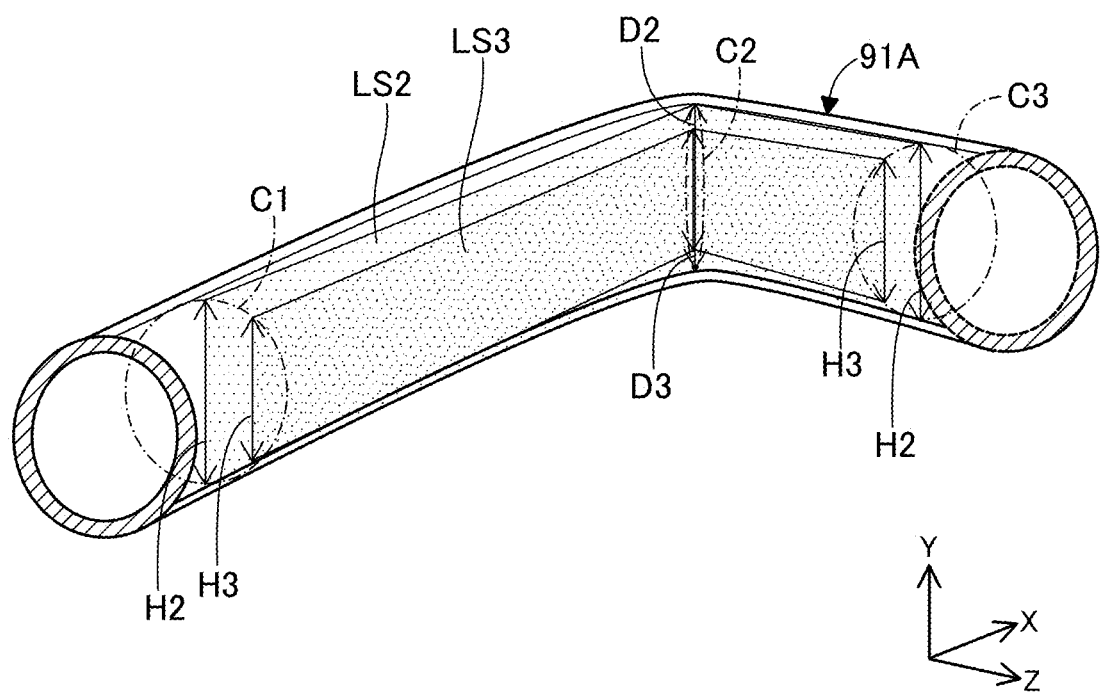
FIG. 12 is a diagram describing a process in the position specification portion of the second embodiment.

FIG. 12 is a diagram describing a process in the position specification portion 52A of the second embodiment. The position specification portion 52A specifies a blood vessel 91A to be displayed as an image from three-dimensional image information Ics using the same method as in the first embodiment. FIG. 12 shows an example of the blood vessel 91A specified by the position specification portion 52A. The blood vessel 91A has a curved shape that extends, from the left to the right in the figure, in the +X-axis direction and then extends in the +X-axis direction, the −Y-axis direction, and the +Z-axis direction.

Next, the position specification portion 52A acquires the transverse cross-section C2 of the specified blood vessels 91A at a position where the amount of change in the shape of the blood vessel 91A is relatively large (hereinafter also referred to as "changing position"). Acquisition of the changing position can be achieved by a known image recognition method. The acquired transverse cross-section C2 represents a curved point, a bent point, a branched point, or the like (hereinafter referred to as "inclined point") of the blood vessel 91A. Further, the position specification portion 52A acquires freely selected transverse cross-sections C1 and C3 located on both sides of the transverse cross-section C2 in the extending direction of the blood vessel 91A. In this manner, the position specification portion 52A of the second embodiment acquires the plurality of transverse cross-sections C1 to C3 from the blood vessel 91A. Although three transverse cross-sections are shown as examples in the figure, the number of transverse cross-sections acquired by the position specification portion 52A can be freely determined.

The position specification portion 52A specifies the position in the blood vessel 91A where the longitudinal cross-section width of the blood vessel 91A is maximum using the acquired transverse cross-sections C1 to C3. Details are the same as in the first embodiment.

Figure 13:
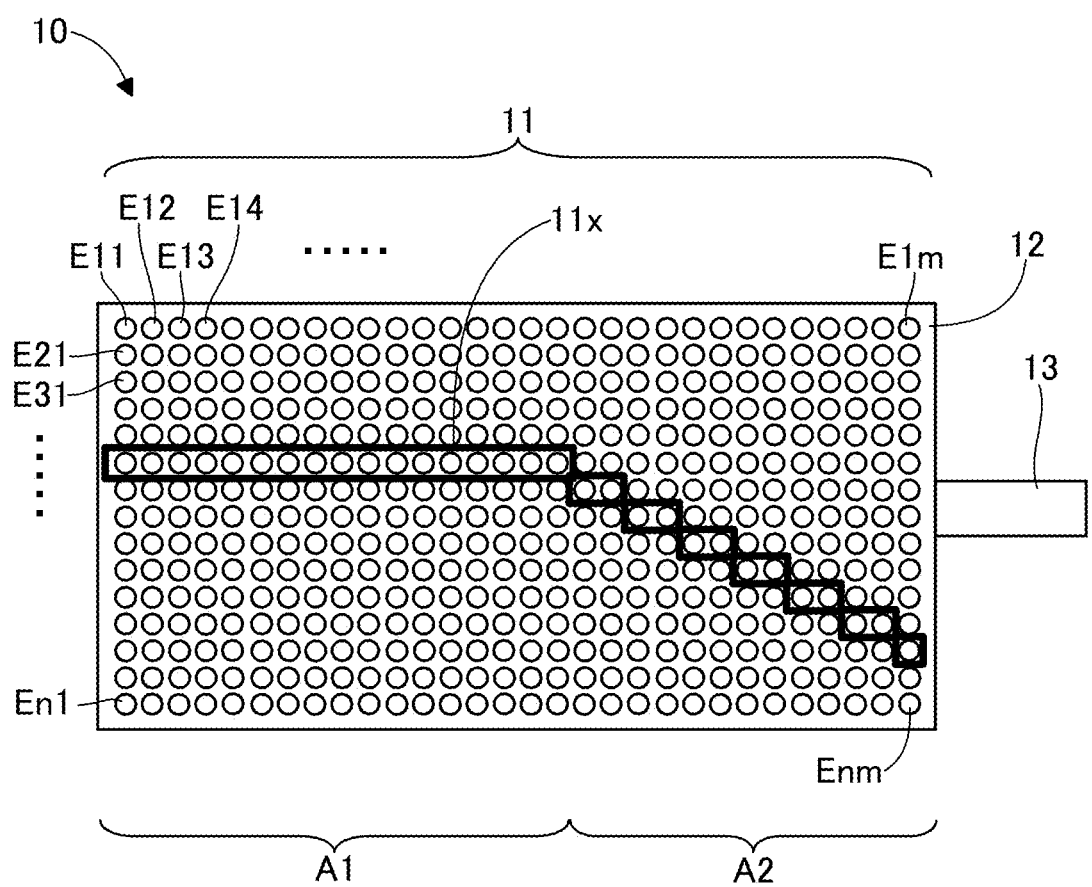
FIG. 13 is a diagram describing a process in the image generation portion of the second embodiment.

FIG. 13 is a diagram describing a process in the image generation portion 53A of the second embodiment. The image generation portion 53A generates an image representing the longitudinal cross-section LS2 of the blood vessel 91A at the position specified by position specification portion 52A (i.e., the position of the width H2 where the width in the Y-axis direction is maximum for each of the transverse cross-sections C1 to C3). In this process, the image generation portion 53A of the present embodiment generates an image skipping the inclined portion of the blood vessel 91A. For example, it is assumed that a distal portion of the catheter 20 is located in front of the inclined portion of the blood vessel 91A (i.e., between the transverse cross-sections C1 and C2) at a certain time t1, and the distal portion of the catheter 20 is located beyond the inclined portion of the blood vessel 91A (i.e., between the transverse cross-sections C2 and C3) at the following time t2. In this case, the image generation portion 53A uses reflected waves received by the ultrasonic sensors 11x positioned in a region A1 among the ultrasonic sensors 11x (FIG. 13: rectangular frame) at the position corresponding to the longitudinal cross-section LS2 to generate and display in the display 60 a two-dimensional image with gradation scales according to the intensity of the reflected wave in each of the ultrasonic sensors 11x at the time t1. Next, the image generation portion 53A uses reflected waves received by the ultrasonic sensors 11x in a region A2 among the ultrasonic sensors 11x (FIG. 13: rectangular frame) at the position corresponding to the longitudinal cross-section LS2 to generate and display in the display 60 the two-dimensional image with gradation scales according to the intensity of the reflected wave in each of the ultrasonic sensors 11x at the time t2.

Figure 14A:
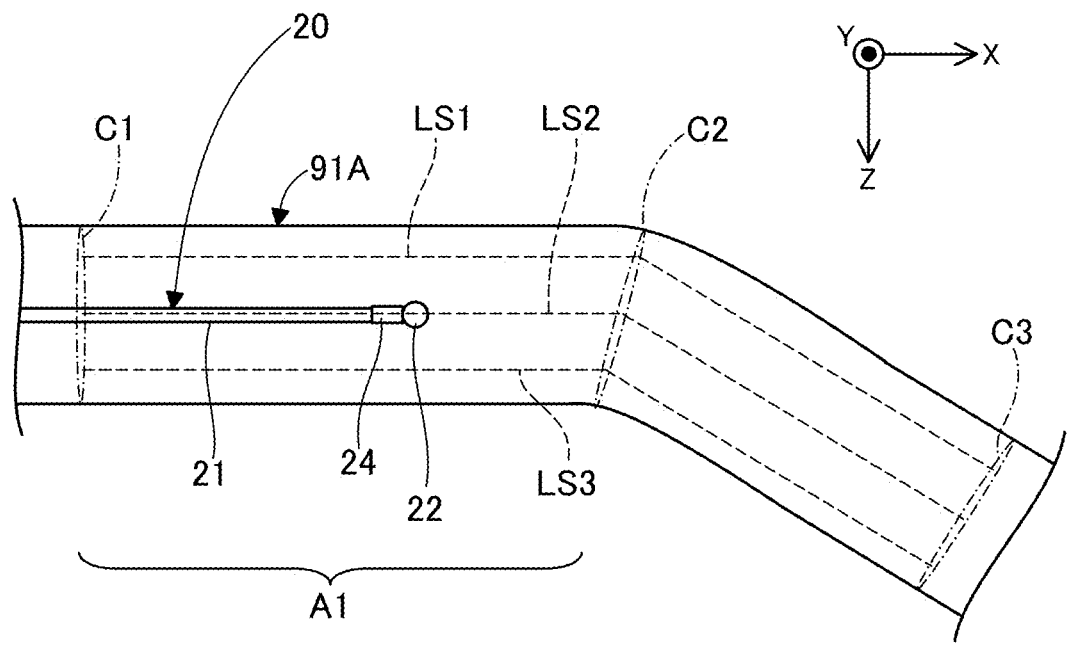
FIGS. 14A and 14B are diagrams illustrating an example of the image displayed in the display portion at time t1.
Figure 14B:
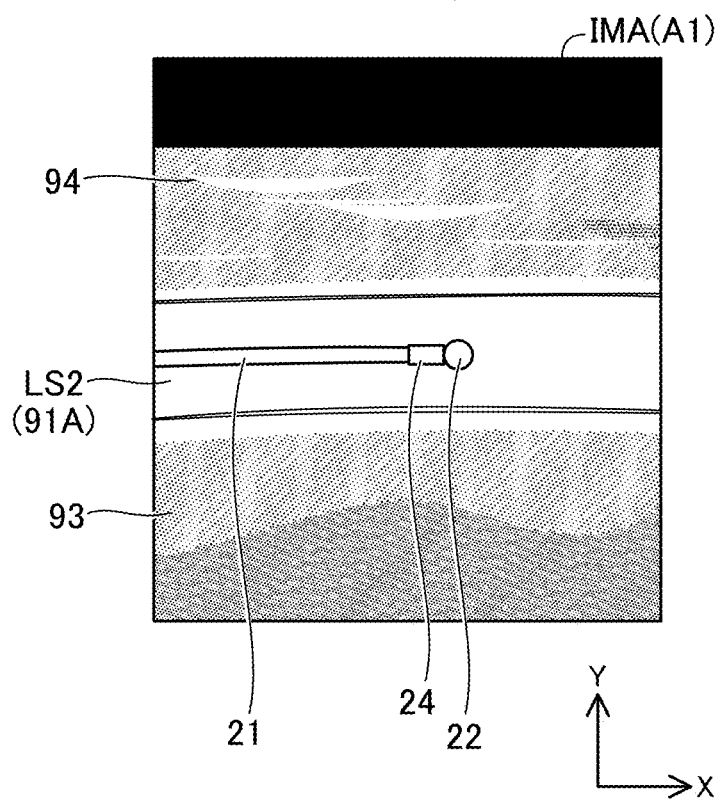

FIGS. 14A and 14B are diagrams illustrating an example of the image displayed in the display 60 at the time t1. FIG. 14A shows the positional relationship between the blood vessel 91A and the catheter 20 viewed from the Y-axis direction, and FIG. 14B shows an example of an image IMA displayed in the display 60 in this situation. The image IMA is a two-dimensional image representing the XY plane including the longitudinal cross-section LS2 as described in the first embodiment. As shown in the figure, when the catheter 20 is advancing near the longitudinal cross-section LS2 of the blood vessel 91A in front of the inclined portion of the blood vessel 91A (i.e., between the transverse cross-sections C1 and C2), the image IMA includes an image of the blood vessel 91A in the region A1 corresponding to the position between the transverse cross-sections C1 and C2, and the catheter 20.

Figure 15A:
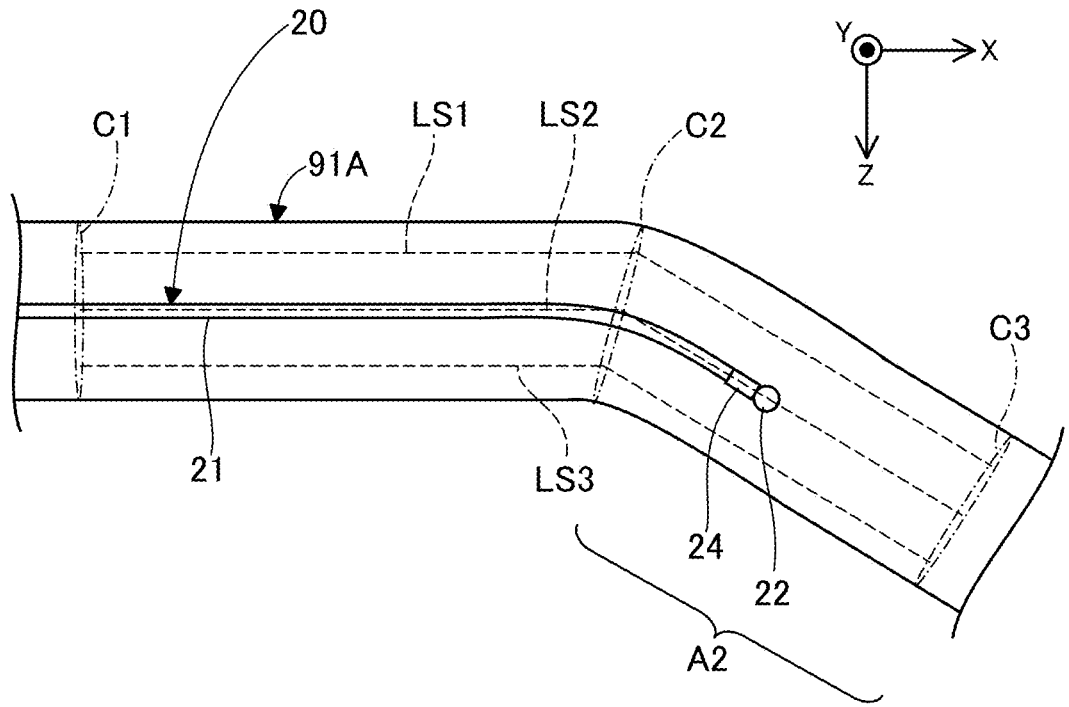
FIGS. 15A and 15B are diagrams illustrating an example of the image displayed in the display portion at time t2.
Figure 15B:
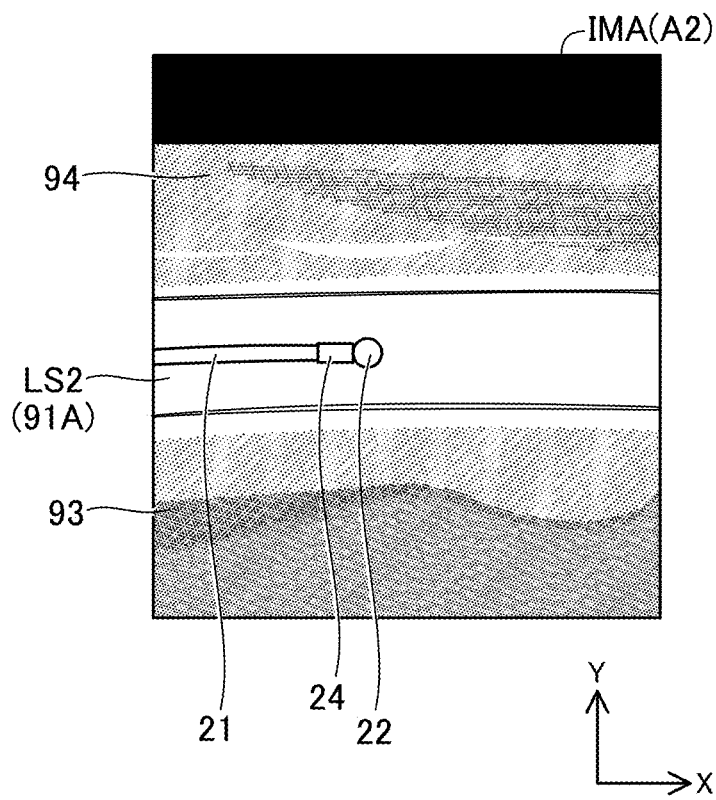

FIGS. 15A and 15B are diagrams illustrating an example of the image displayed in the display 60 at the time t2. The configurations in FIGS. 15A and 15B are the same as those in FIGS. 14A and 14B. As shown in the figure, when the catheter 20 is advancing near the longitudinal cross-section LS2 of the blood vessel 91A beyond the inclined portion of the blood vessel 91A (i.e., between the transverse cross-sections C2 and C3), the image IMA includes an image of the blood vessel 91A in the region A2 corresponding to the position between the transverse cross-sections C2 and C3, and the catheter 20. In this process, as shown in FIG. 15B, the image generation portion 53A performs correction of the two-dimensional image so that the blood vessel 91A always appears to extend linearly in the image IMA regardless of the actual direction of the blood vessel 91A. This correction can be performed by a known tilt correction process.

As described above, the image display device 1A of the second embodiment can generate and display the image IMA corresponding to the shape change such as curving or branching of the blood vessel 91A (biological tube). Thus, the operator can determine that the catheter 20 is not advancing along the shape of the blood vessel 91A when a part of the catheter 20 on the distal side disappears from the image IMA shown in FIGS. 14B and 15B. In this case, the operator once pulls back the catheter 20, changes the direction of the catheter 20 so that the entire catheter 20 appears in the image IMA, and then pushes the catheter 20 forward. In this manner, the catheter 20 can be delivered along the shape of the blood vessel 91A, making it possible to prevent the catheter 20 from colliding with the inner wall of the blood vessel 91A and improve the safety of the procedure.

As described above, the position specification portion 52A may acquire the transverse cross-section C2 at the position where the amount of change in the shape of the blood vessel 91A is relatively large (changing position), acquire the transverse cross-sections C1 and C3 located on both sides of the transverse cross-section C2 as a reference, and specify the position where the longitudinal cross-section width of the blood vessel 91A is maximum by using the information on these transverse cross-sections C1 to C3. Further, the image generation portion 53A may generate the image IMA using the information from any of the ultrasonic sensors E11 to Enm among the plurality of ultrasonic sensors 11 of the ultrasonic sensor array 10. Also, in this manner, the same effect as in the first embodiment can be obtained, and the safety of the procedure can be improved. Further, in the image display device 1A of the second embodiment, as shown in FIG. 15B, the image generation portion 53A corrects the two-dimensional image so that the blood vessel 91A always appears to extend linearly in the image IMA. Thus, the operator is only required to operate the catheter 20 such that the catheter 20 is positioned at the center of the blood vessel 91A in the image IMA without paying attention to the actual direction of the blood vessel 91A. As a result, according to the image display device 1A of the second embodiment, the procedure can be easily performed.

Third Embodiment

Figure 16A:
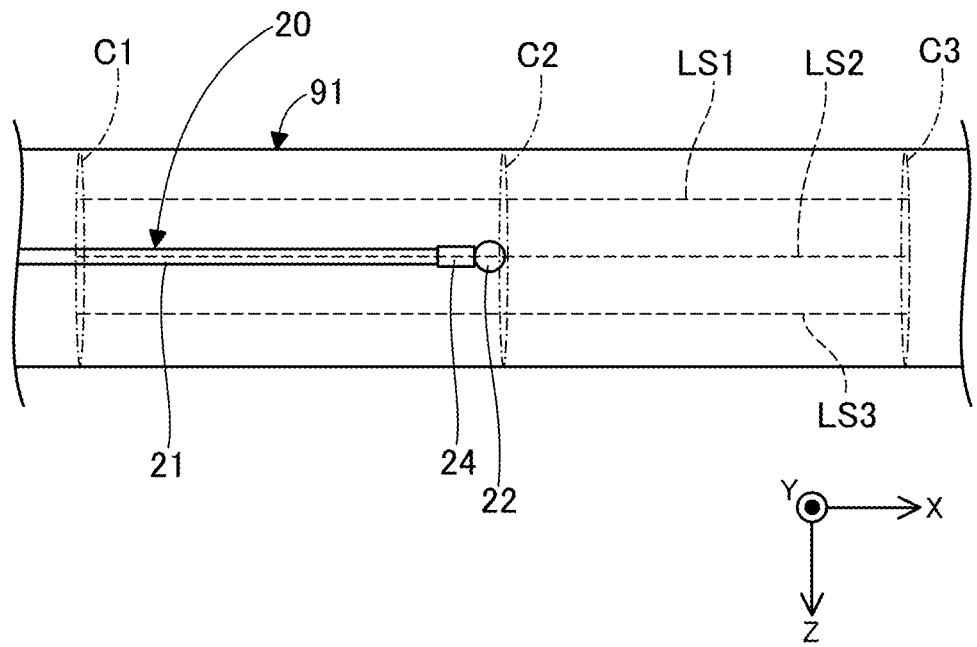
FIGS. 16A and 16B are diagrams illustrating an example of the image, displayed in the display portion, of a third embodiment.
Figure 16B:
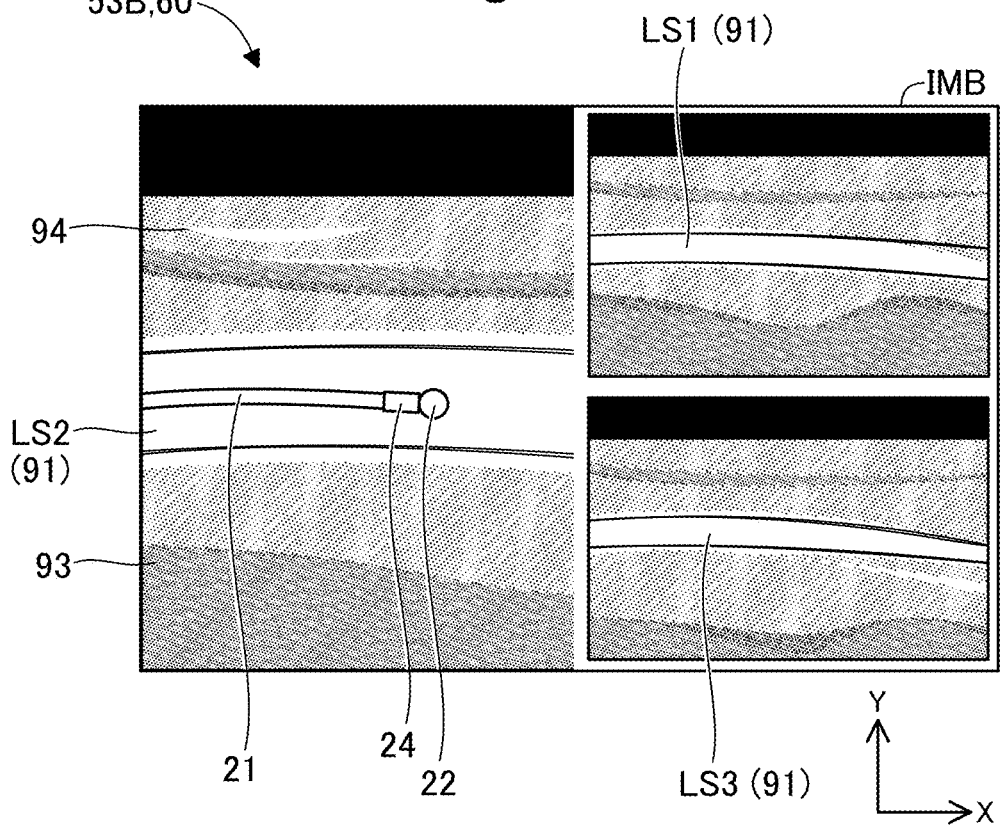

FIGS. 16A and 16B are diagrams illustrating an example of the image, displayed in the display 60, of a third embodiment. FIG. 16A shows the positional relationship between the blood vessel 91 and the catheter 20 viewed from the Y-axis direction, and FIG. 16B shows an example of an image IMB displayed in the display 60 in this situation. The image display device 1 of the third embodiment can generate and display an image representing the longitudinal cross-sections at a plurality of positions of the biological tube. The computer 50 in the image display device 1 of the third embodiment includes an image generation portion 53B instead of the image generation portion 53 in the configuration of the first embodiment.

As shown in FIG. 16B, the image IMB generated by the image generation portion 53A includes, on the left side, an image representing the longitudinal cross-section LS2 at the position where the longitudinal cross-section width of the blood vessel 91 is maximum. Further, the image IMB includes, on the upper right side, an image representing a longitudinal cross-section LS1 at a position where the longitudinal cross-section width of the blood vessel 91 is not maximum, and, similarly on the lower right side, an image representing a longitudinal cross-section LS3 at a position where the longitudinal cross-section width of the blood vessel 91 is not maximum. As shown in FIG. 16A, when the catheter 20 is advancing near the longitudinal cross-section LS2 of the blood vessel 91, the catheter 20 is included in the image on the left side of the image IMB.

Figure 17A:
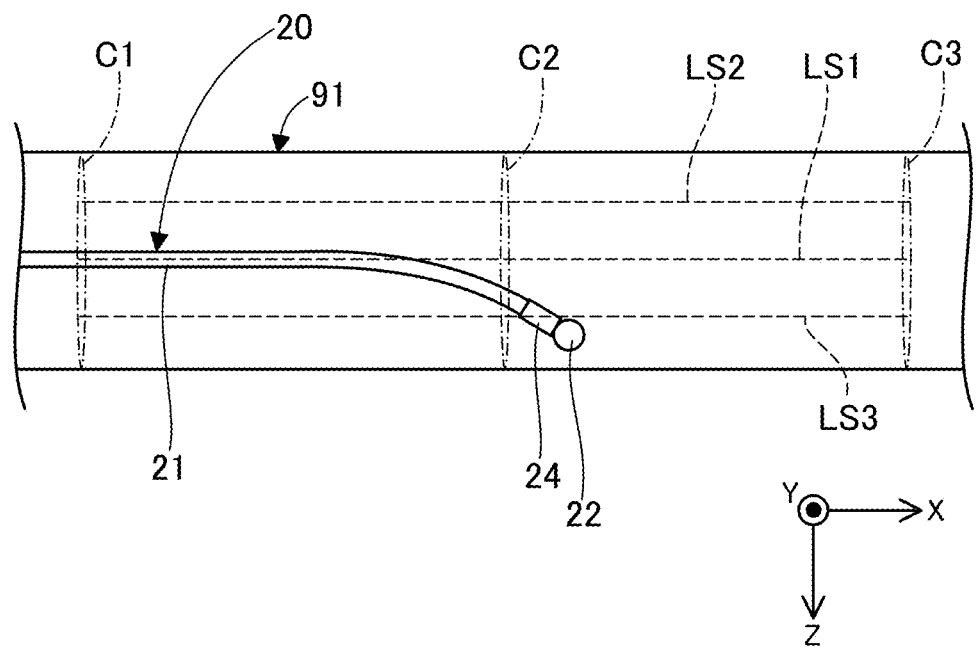
FIGS. 17A and 17B are diagrams illustrating another example of the image, displayed in the display portion, of the third embodiment.
Figure 17B:
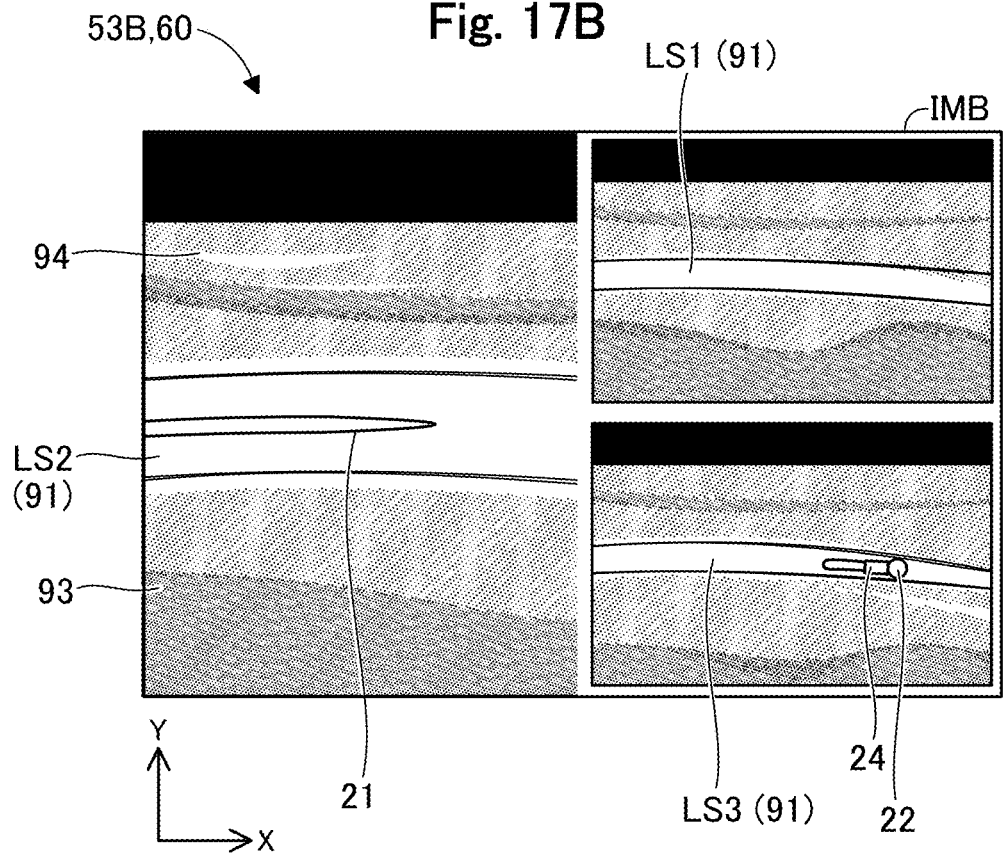

FIGS. 17A and 17B are diagrams illustrating another example of the image, displayed in the display 60, of the third embodiment. The configurations in FIGS. 17A and 17B are the same as those in 16A and 16B. As shown in FIG. 17A, it is assumed that a part of the catheter 20 on the proximal side is along the longitudinal cross-section LS2 and a part on the distal side is curved from the longitudinal cross-section LS2 to the direction of the longitudinal cross-section LS3. In such a case, as shown in FIG. 17B, a part of the catheter 20 on the proximal side is included in the image on the left side of the image IMB and a part of the catheter 20 on the distal side is included in the image on the lower right side of the image IMB.

As described above, the image generation portion 53B may generate the image IMB including, in addition to the image representing the longitudinal cross-section LS2 of the blood vessel 91 (biological tube) at the position specified by the position specification portion 52, an image representing the longitudinal cross-sections LS1 and LS3 of the blood vessel 91 at other positions. Also, in this manner, the same effect as in the first embodiment can be obtained. Further, according to the image display device 1 of the third embodiment, the operator can notice that the position of the catheter 20 is shifted by referring to the image representing the longitudinal cross-sections LS1 and LS3 of the blood vessel 91 at other positions.

Fourth Embodiment

Figure 18:
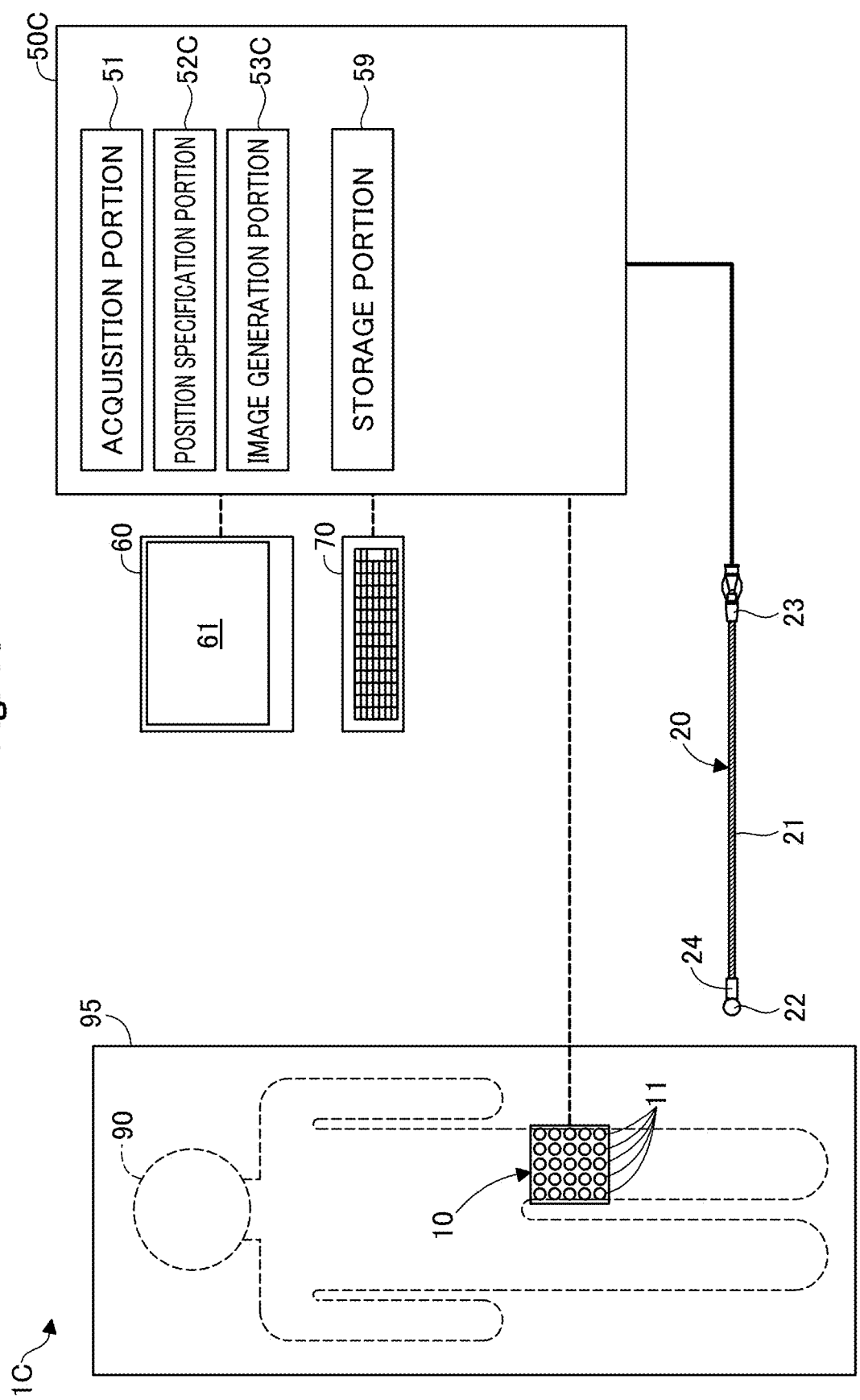
FIG. 18 is an explanatory diagram illustrating an example of a configuration of the image display device of a fourth embodiment.

FIG. 18 is an explanatory diagram illustrating an example of a configuration of an image display device 1C of a fourth embodiment. The image display device 1C of the fourth embodiment differs from that of the first embodiment in the method of specifying the position where the longitudinal cross-section width of the biological tube is maximum. The image display device 1C includes a computer 50C instead of the computer 50 in the configuration of the first embodiment. The computer 50C includes a position specification portion 52C instead of the position specification portion 52 and an image generation portion 53C instead of the image generation portion 53.

Figure 19:
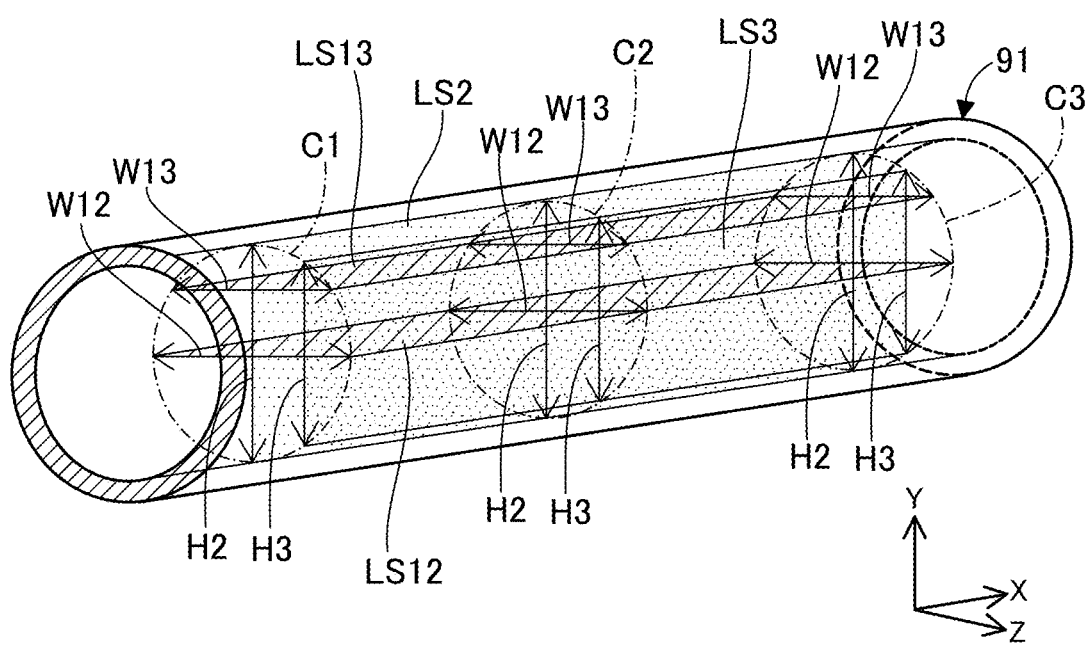
FIG. 19 is a diagram describing a process in the position specification portion of the fourth embodiment.

FIG. 19 is a diagram describing a process in the position specification portion 52C of the fourth embodiment. Using the same method as in the first embodiment, the position specification portion 52C specifies the blood vessel 91 to be displayed as an image from the three-dimensional image information Ics and acquires the freely selected transverse cross-sections C1 to C3. FIG. 19 shows an example of the blood vessel 91 specified by the position specification portion 52C. Next, the position specification portion 52C specifies the position where the longitudinal cross-section width of the blood vessel 91 is maximum in the blood vessel 91 using the acquired transverse cross-sections C1 to C3 in blood vessel 91. Specifically, the position specification portion 52C specifies the maximum width (a width W12 in the example of FIG. 19) among widths W11 to W1$x$ (where x is any natural number) in the Z-axis direction for each of the acquired transverse cross-sections C1 to C3. In the fourth embodiment, the position of the width W12 specified in this process corresponds to the position where the longitudinal cross-section width of the blood vessel 91 is maximum.

The image generation portion 53C generate an image representing a longitudinal cross-section LS12 of the blood vessel 91 at the position specified by the position specification portion 52C (i.e., the position of W12 where the width in the Z-axis direction is maximum for each of the transverse cross-sections C1 to C3). Then, the image generation portion 53C causes the display 60 to display the generated image. Note that FIG. 19 shows the widths H11 to H13 and the longitudinal cross-sections LS2 and LS3 (hatched with dots) used in the first embodiment in addition to the widths W12 and W13 and the longitudinal cross-sections LS12 and LS13 (hatched with diagonal lines) described above. As shown in FIG. 19, the longitudinal cross-sections LS12 and LS13 of the fourth embodiment are planes that perpendicularly intersect the longitudinal cross-sections LS2 and LS3 of the first embodiment.

Figure 20A:
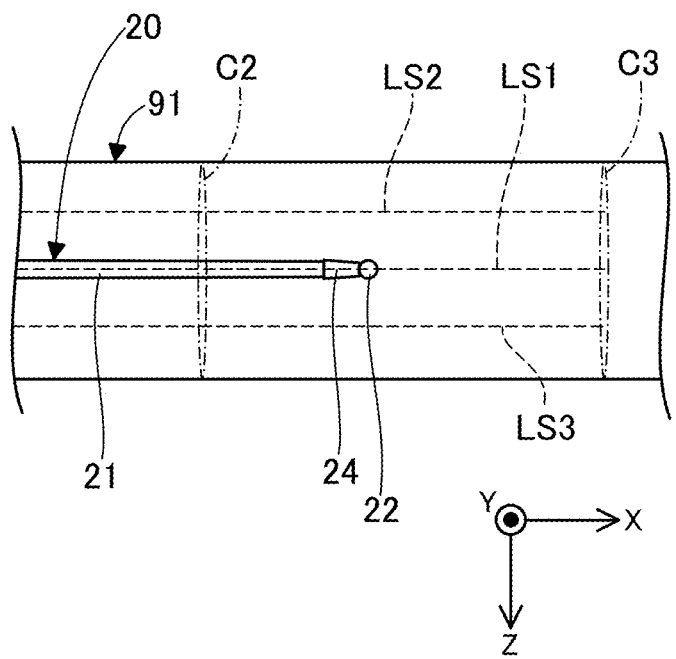
FIGS. 20A, 20B, and 20C are diagrams illustrating an example of the image, displayed in the display portion, of the fourth embodiment.
Figure 20B:
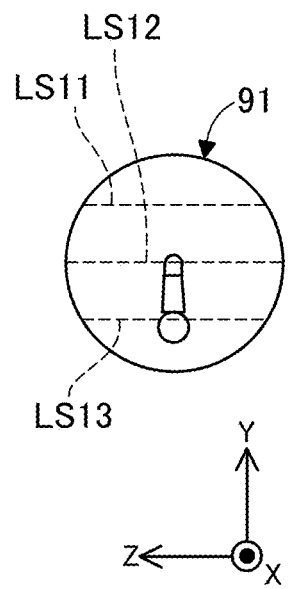
Figure 20C:
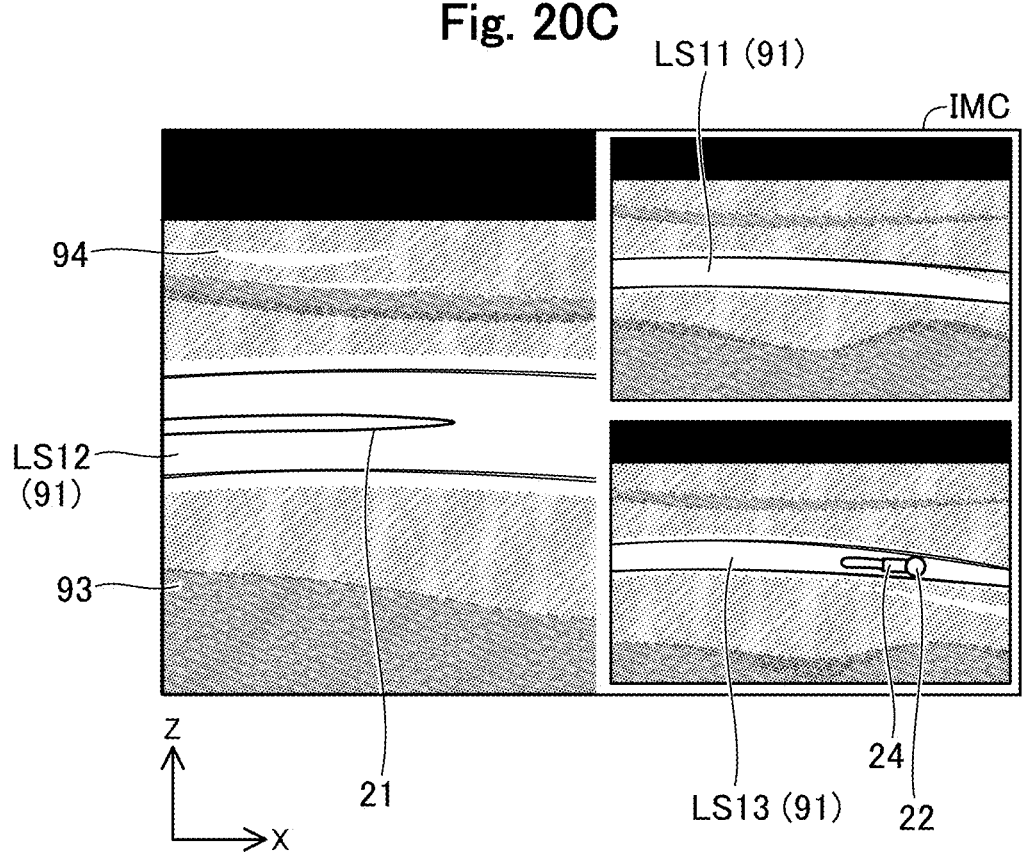

FIGS. 20A, 20B, and 20C are diagrams illustrating an example of the image, displayed in the display 60, of the fourth embodiment. FIG. 20A shows the positional relationship between the blood vessel 91 and the catheter 20 viewed from the Y-axis direction, FIG. 20B shows the positional relationship between the blood vessel 91 and the catheter 20 viewed from the X-axis direction, and FIG. 20C shows an example of an image IMC displayed in the display 60 in this situation. As shown in FIG. 20C, the image IMC is a two-dimensional image representing an XZ plane including the longitudinal cross-sections LS11 to LS13. The image IMC includes, on the left side, an image representing the longitudinal cross-section LS12 at the position where the longitudinal cross-section width of the blood vessel 91 is maximum. Further, the image IMC includes, on the upper right side, an image representing the longitudinal cross-section LS11 at a position where the longitudinal cross-section width of the blood vessel 91 is not maximum, and, similarly on the lower right side, an image representing the longitudinal cross-section LS13 at a position where the longitudinal cross-section width of the blood vessel 91 is not maximum.

As shown in FIG. 20B, it is assumed that a part of the catheter 20 on the proximal side is along the longitudinal cross-section LS12 and a part on the distal side is curved from the longitudinal cross-section LS12 to the direction of the longitudinal cross-section LS13. In such a case, as shown in FIG. 20C, the part of the catheter 20 on the proximal side is included in the image on the left side of the image IMC and the part of the catheter 20 on the distal side is included in the image on the lower right side of the image IMC.

As described above, the position specification portion 52C may specify the position where the longitudinal cross-section width of the blood vessel 91 (biological tube) is maximum using the Z-axis direction, and the image generation portion 53C may generate the image IMC including the longitudinal cross-section LS12 in the Z-axis direction. Further, the position specification portion 52C may perform both the position specification using the Y-axis direction described in the first embodiment and the position specification using the Z-axis direction described in the fourth embodiment. In this case, the image generation portion 53C may generate the image IMC including the longitudinal cross-section LS2 in the Y-axis direction described in the first embodiment and the longitudinal cross-section LS12 in the Z-axis direction described in the fourth embodiment. Further, the position specification portion 52C may perform the same process using any direction inclined with respect to the Y-axis and Z-axis. Also, in this manner, the same effect as in the first embodiment and the third embodiment can be obtained.

Fifth Embodiment

Figure 21A:
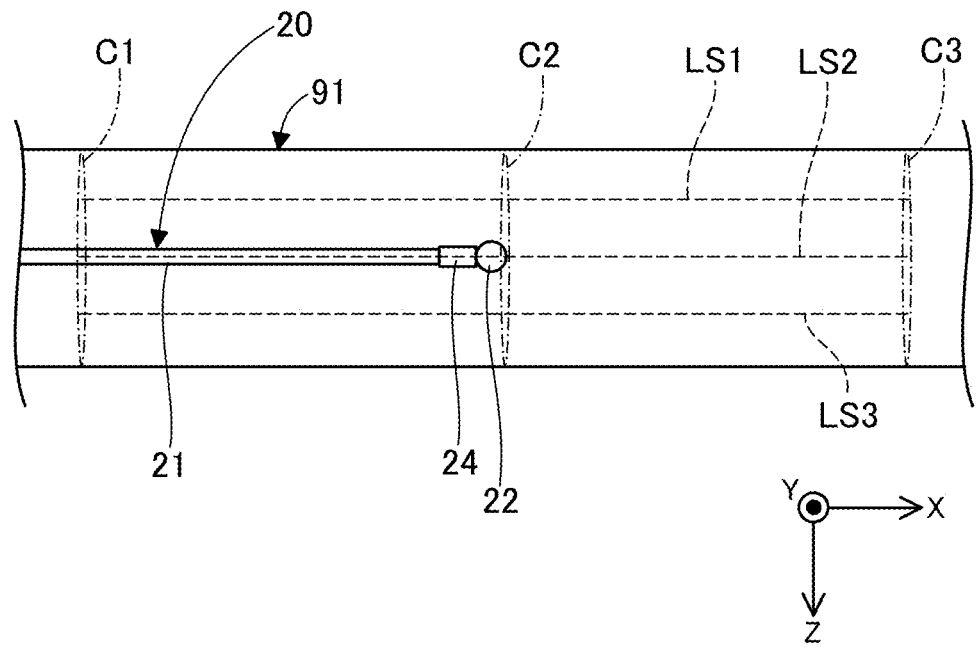
FIGS. 21A and 21B are diagrams illustrating an example of the image, displayed in the display portion, of a fifth embodiment.
Figure 21B:
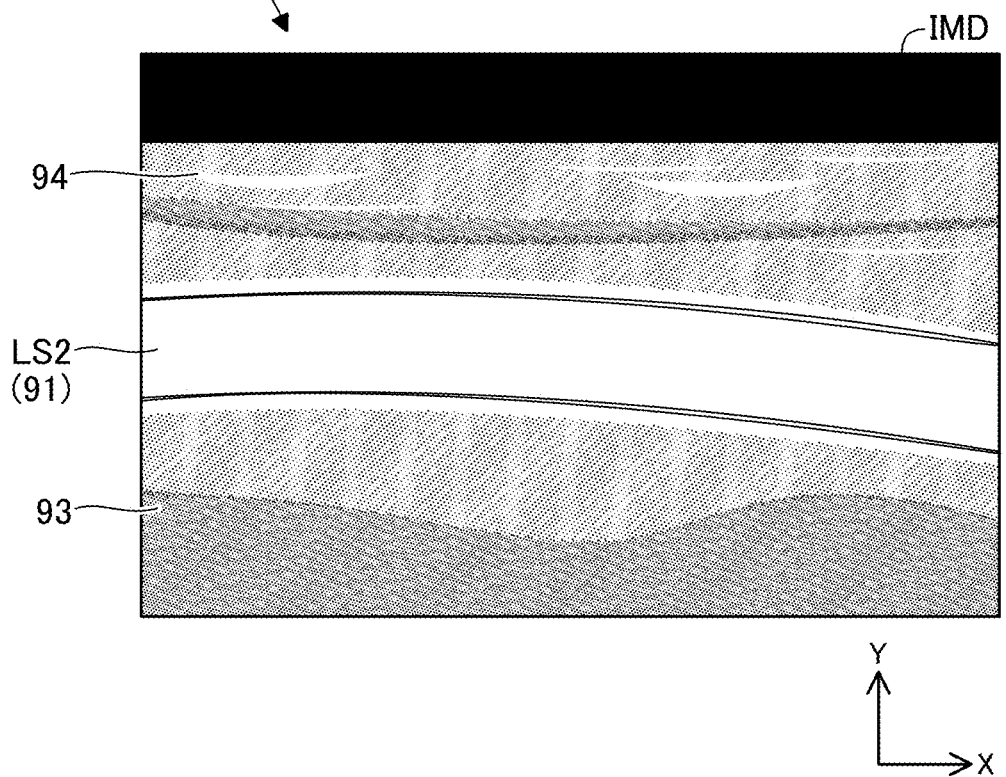

FIGS. 21A and 21B are diagrams illustrating an example of the image, displayed in the display 60, of a fifth embodiment. FIG. 21A shows the positional relationship between the blood vessel 91 and the catheter 20 viewed from the Y-axis direction, and FIG. 21B shows an example of an image IMD displayed in the display 60 in this situation. The image display device 1 of the fifth embodiment generates and displays an image representing the longitudinal cross-section of the biological tube that does not include the catheter 20. The computer 50 of the image display device 1 of the fifth embodiment includes an image generation portion 53D instead of the image generation portion 53 in the configuration of the first embodiment. The image generation portion 53D generates the image IMD including the longitudinal cross-section LS2 of the blood vessel 91 at the position H2 specified by the position specification portion 52 and not including the catheter 20 and causes the display 60 to display the image. Thus, as shown in FIG. 21A, even if the catheter 20 is advancing near the longitudinal cross-section LS2 of the blood vessel 91, the catheter 20 is not included in the image IMD as shown in FIG. 21B. Also, in this manner, the same effect as in the first embodiment can be obtained.

Modification of Present Embodiment

In the above embodiments, a part of the configuration achieved by the hardware may be replaced with software, and conversely, a part of the configuration achieved by the software may be replaced with hardware. Further, the present invention is not limited to the above embodiments and can be implemented in various aspects without departing from the scope of the invention. For example, the following modifications are possible.

Modification 1

In the above first to fifth embodiments, the configurations of the image display devices 1, 1A, and 1C have been described as examples. However, the configuration of the image display device 1 can be modified in various ways. For example, in the image display device 1, at least a part of the ultrasonic sensor array 10, the computer 50, the display 60, and the operation portion 70 may be configured as an integrated device. For example, in the ultrasonic sensor array 10, the plurality of ultrasonic sensors 11 are disposed in the belt-shaped body 12. However, the plurality of ultrasonic sensors 11 may be provided on the inner surface of a wearable object such as a hat, the inner surface of clothing such as a gown, the inner surface of a pad placed on the body surface, or the like. For example, although the plurality of ultrasonic sensors 11 are disposed on the entire inner surface of the belt-shaped body 12, the plurality of ultrasonic sensors 11 may be disposed on a part of the inner surface of the belt-shaped body 12.

Modification 2

In the above first to fifth embodiments, examples of the processes in the position specification portions 52, 52A, and 52C and the processes in the image generation portions 53 and 53A to 53D have been described. However, the processes in the position specification portion 52 and the image generation portion 53 can be modified in various ways. For example, the position specification portion 52 may acquire an operator's instruction via the operation portion 70 regarding the number and setting location of the transverse cross-sections C1 to C3 and perform the process according to the instruction. For example, the image generation portion 53 may acquire an operator's instruction via the operation portion 70 to determine whether the longitudinal cross-section to be displayed in the image IM to be generated has the configuration described in the first, second, or fifth embodiment or the configuration described in the third or fourth embodiment and perform the process according to the instruction.

Modification 3

The configurations of the image display devices 1, 1A, and 1C of the first to fifth embodiments described above and the configurations of the modifications 1 and 2 described above may be appropriately combined. For example, in the configuration for generating and displaying the image corresponding to the shape change of the biological tube described in the second embodiment, the image including the plurality of longitudinal cross-sections described in the third embodiment may be generated, the image including the longitudinal cross-section in the Z-axis direction described in the fourth embodiment may be generated, or the image not including the medical device described in the fifth embodiment may be generated.

The present aspect has been described based on the embodiments and modifications. However, the above-mentioned embodiments are intended to facilitate understanding of the present aspect and are not intended to limit the present aspect. In some instances, as would be apparent to one of skill in the art as of the filing of the present application, features, characteristics, and/or elements described in connection with a particular embodiment may be used singly or in combination with features, characteristics, and/or elements described in connection with other embodiments unless otherwise indicated. The present aspect can be modified or improved without departing from the gist and scope of the claims and includes equivalents thereof. Further, the technical features may be omitted as appropriate unless they are described as essential in the present specification.

DESCRIPTION OF REFERENCE NUMERALS 1, 1A, 1C: Image display device
10: Ultrasonic sensor array
11, 11x: Ultrasonic sensor
12: Belt-shaped body
13: Band
20: Catheter
21: Shaft
22: Distal tip
23: Connector
24: Marker
50, 50A, 50C: Computer
51: Acquisition portion
52, 52A, 52C: Position specification portion
53, 53A to 53D: Image generation portion
59: Storage portion
60: Display
61: Display screen
70: Input device
90: Human body
91, 91A: Blood vessel
92: Bone
93: Muscle
94: Fat
95: Bed

What is claimed is:

1. An image display device comprising:
circuitry configured to:
acquire, from a human body, three-dimensional image information on an inside of the human body including a biological tube using a plurality of ultrasonic sensors;
specify a position, by using transverse cross-section information on the biological tube included in the three-dimensional image information, wherein the position specified is at a center of an inner diameter of the biological tube in a transverse cross-section;
generate an image representing a longitudinal cross-section of the biological tube at the position specified; and
output the image generated to a display,
wherein the three-dimensional image information includes three-dimensional image information on a medical device inserted into a biological lumen and a position of the medical device in the transverse cross-section; and
in a case where the position of the medical device in the transverse cross-section is at the position specified, the circuitry is configured to generate the image including the longitudinal cross-section of the biological tube and the medical device, and
in a case where the medical device in the transverse cross-section is not at the position specified, the circuitry is configured to generate the image including the longitudinal cross-section of the biological tube but not including the medical device.

2. The image display device according to claim 1, wherein the plurality of ultrasonic sensors is configured to surround the human body.

3. The image display device according to claim 2, wherein the plurality of ultrasonic sensors are ultrasonic elements configured to be disposed inside an entire circumference of a belt-shaped body configured to surround the human body.

4. The image display device according to claim 3, wherein the circuitry is configured to:
specify, at each of the plurality of positions of the biological tube along an extending direction, the position of the inner diameter of the biological tube; and
generate the images representing the longitudinal cross-sections of the biological tube at the plurality of positions identified.

5. The image display device according to claim 1, wherein the circuitry is configured to:
specify, at each of the plurality of positions of the biological tube along an extending direction, the position of the inner diameter of the biological tube; and
generate the images representing the longitudinal cross-sections of the biological tube at the plurality of positions identified.

6. The image display device according to claim 1, wherein, when an acquired transverse cross-section information on the biological tube indicates the biological tube is an inclined portion, the circuitry is configured to generate an image that does not include the inclined portion.

7. The image display device according to claim 1, wherein the circuitry is further configured to
specify a shifted position offset from the position of the inner diameter,
generate a shifted image representing the longitudinal cross-section of the biological tube at the shifted position specified, and
output the shifted image to the display to be displayed along with the image.

8. The image display device according to claim 7, wherein the circuitry is further configured to
specify two shifted positions offset from the position of the inner diameter of the biological tube,
generate two shifted images representing the longitudinal cross-section of the biological tube at the two shifted positions specified, and
output the two shifted images to the display to be displayed along with the image.

9. The image display device according to claim 8, wherein the shift is along a width of the longitudinal cross-section.

10. The image display device according to claim 7, wherein the shifted image is along a direction perpendicular to the longitudinal cross-section.

11. An image display method comprising:
acquiring, from a human body, three-dimensional image information on an inside of the human body including a biological tube using a plurality of ultrasonic sensors;
specifying a position, using transverse cross-section information on the biological tube included in the three-dimensional image information, wherein the position specified is at a center of an inner diameter of the biological tube in a transverse cross-section;
generating an image representing a longitudinal cross-section of the biological tube at the specified position;
outputting the generated image to a display, wherein the three-dimensional image information includes three-dimensional image information on a medical device inserted into a biological lumen and a position of the medical device in the transverse cross-section;
determining whether the position of the medical device is present at the position specified; and in response to the medical device being at the position specified, generating the image including the longitudinal cross-section of the biological tube and the medical device, and in response to the medical device not being present at the position specified by, generating the image including the longitudinal cross-section of the biological tube but not including the medical device.

12. A non-transitory computer readable storage device having computer readable instructions that when executed by circuitry cause the circuitry to:

acquire, from a human body, three-dimensional image information on an inside of the human body including a biological tube using a plurality of ultrasonic sensors;

specify a position, using transverse cross-section information on the biological tube included in the three-dimensional image information, wherein the position specified is at a center of an inner diameter of the biological tube in a transverse cross-section;

generate an image representing a longitudinal cross-section of the biological tube at the position specified; and output the image generated to a display, wherein the three-dimensional image information includes three-dimensional image information on a medical device inserted into a biological lumen and a position of the medical device in the transverse cross-section; and in a case where the position of the medical device in the transverse cross-section is at the position specified, the circuitry is configured to generate the image including the longitudinal cross-section of the biological tube and the medical device, and in a case where the medical device in the transverse cross-section is not at the position specified, the circuitry is configured to generate the image including the longitudinal cross-section of the biological tube but not including the medical device.

13. The non-transitory computer readable storage according to claim 12, wherein the circuitry is further configured to in a case where a first portion of the medical device is present at the specified position in the transverse cross-section and a second portion of the medical device is not present at the specified position in the transverse cross-section, generate the image including the longitudinal cross-section of the biological tube and the first portion of the medical device, but not including the second portion of the medical device.

14. The image display device according to claim 1, wherein the circuitry is further configured to in a case where a first portion of the medical device is present at the specified position in the transverse cross-section and a second portion of the medical device is not present at the specified position in the transverse cross-section, generate the image including the longitudinal cross-section of the biological tube and the first portion of the medical device, but not including the second portion of the medical device.

15. The image display method according to claim 11, wherein the method further includes determining whether a first portion of the medical device is present at the specified position in the transverse cross-section and a second portion of the medical device is not present at the specified position in the transverse cross-section; and in response to the first portion of the medical device being present at the specified position in the transverse cross-section and the second portion of the medical device not being present at the specified position in the transverse cross-section, generating the image including the longitudinal cross-section of the biological tube and the first portion, but not including the second portion of the medical device.

* * * * *